(12) United States Patent
Sengupta et al.

(10) Patent No.: US 11,554,175 B2
(45) Date of Patent: Jan. 17, 2023

(54) EVALUATION AND OPTIMIZATION OF SUPRAMOLECULAR THERAPEUTICS

(71) Applicant: AKAMARA THERAPEUTICS, INC., Philadelphia, PA (US)

(72) Inventors: Shiladitya Sengupta, Cambridge, MA (US); Sudip Roy, Delhi (IN); Prithvi Raj Pandey, Delhi (IN)

(73) Assignee: AKAMARA THERAPEUTICS, INC., Philadelphia, PA (US)

(*) Notice: Subject to any disclaimer, the term of this patent is extended or adjusted under 35 U.S.C. 154(b) by 982 days.

(21) Appl. No.: 16/311,484

(22) PCT Filed: Jul. 5, 2017

(86) PCT No.: PCT/US2017/040699
§ 371 (c)(1),
(2) Date: Dec. 19, 2018

(87) PCT Pub. No.: WO2018/009527
PCT Pub. Date: Jan. 11, 2018

(65) Prior Publication Data
US 2019/0231894 A1      Aug. 1, 2019

Related U.S. Application Data

(60) Provisional application No. 62/358,297, filed on Jul. 5, 2016.

(51) Int. Cl.
*A61K 47/68* (2017.01)
*A61P 35/00* (2006.01)
*A61K 47/60* (2017.01)
*G16B 40/00* (2019.01)
*G16C 20/50* (2019.01)
*G16B 15/30* (2019.01)
*A61K 31/337* (2006.01)
*G16B 15/00* (2019.01)
*G16C 10/00* (2019.01)
*G16B 15/20* (2019.01)

(52) U.S. Cl.
CPC ........ *A61K 47/6803* (2017.08); *A61K 31/337* (2013.01); *A61K 47/60* (2017.08); *A61P 35/00* (2018.01); *G16B 15/30* (2019.02); *G16B 40/00* (2019.02); *G16C 20/50* (2019.02); *G16B 15/00* (2019.02); *G16B 15/20* (2019.02); *G16C 10/00* (2019.02)

(58) Field of Classification Search
None
See application file for complete search history.

(56) References Cited

U.S. PATENT DOCUMENTS

2012/0116742 A1   5/2012   Prakash et al.
2015/0193575 A1   7/2015   Houghton et al.

FOREIGN PATENT DOCUMENTS

WO     2015/148126 A1     10/2015

*Primary Examiner* — Michael L Borin
(74) *Attorney, Agent, or Firm* — Nixon Peabody LLP; David S. Resnick; Ravinderjit S. Braich

(57) ABSTRACT

The disclosure provides a process of designing and optimizing supramolecular therapeutics. The disclosure also provides a method for designing and optimizing antibody drug conjugates.

2 Claims, 22 Drawing Sheets

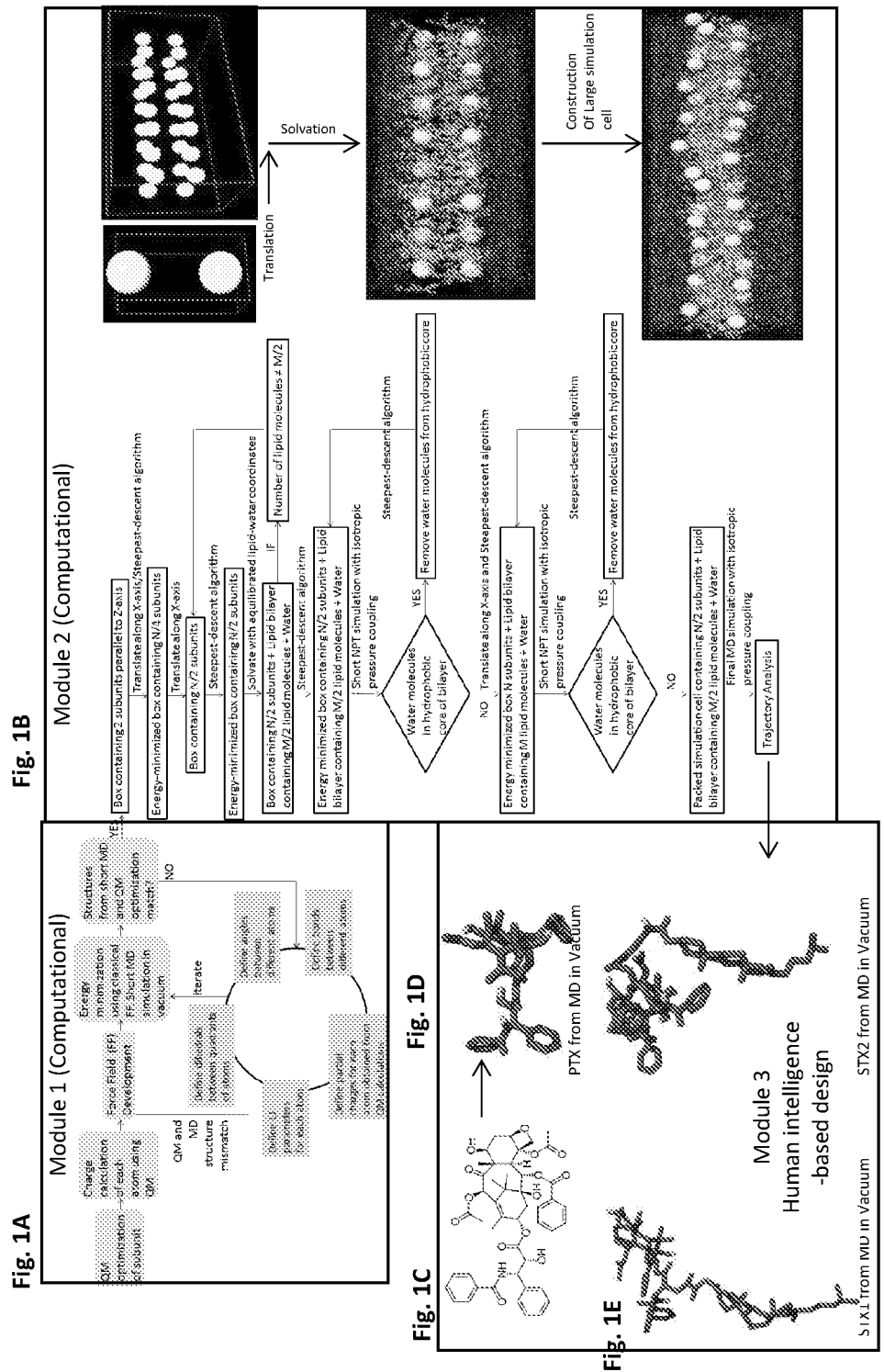

FIG. 2A Schematic diagram of tilt angle calculation

FIG. 2B Distribution vs Angle (degrees); PTX, STX

FIG. 2C Angle between bond vector and z-axis
$$S_{cd} = \left\langle \frac{3\cos^2\theta - 1}{2} \right\rangle$$

FIG. 2D -Scd vs Atom; Pure SOPC, SOPC + PTX, SOPC + STX

FIG. 2E Schematic representation of the unit volume

FIG. 2F Probability vs Number of water molecules/volume; PTX, STX

FIG. 2G Occurance vs Cluster size

CBZ and SCBZ from MD in Vacuum

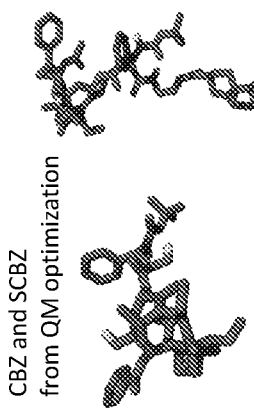
FIG. 5A
FIG. 5B
FIG. 5C
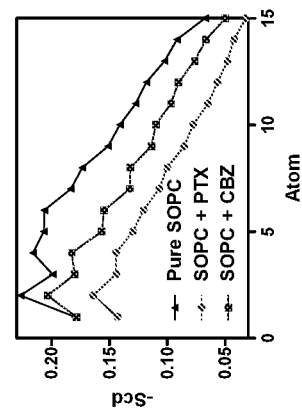
FIG. 5E
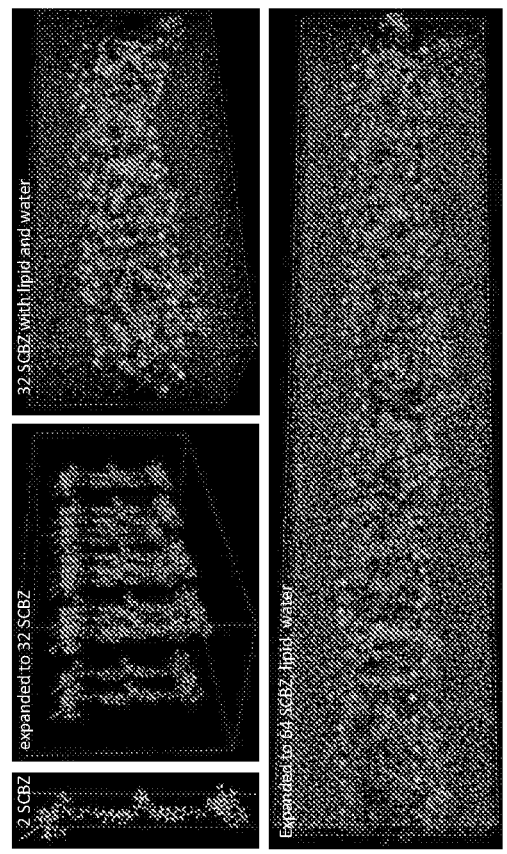
FIG. 5D

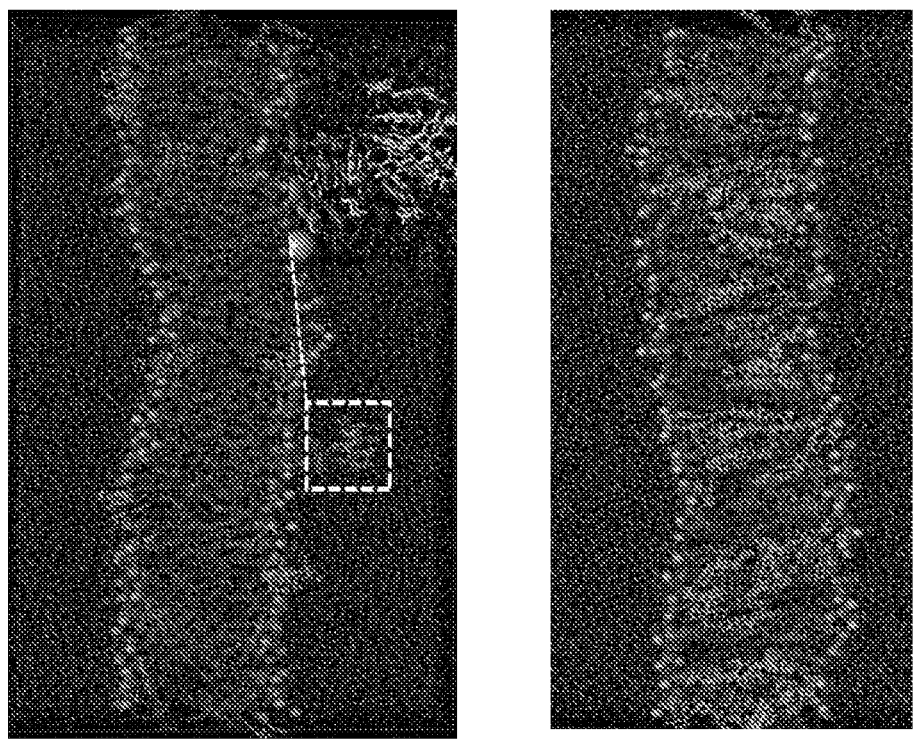
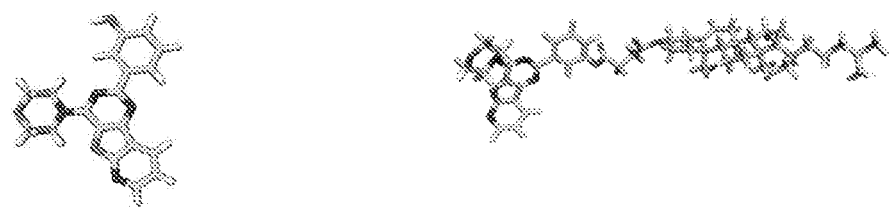
FIG. 6

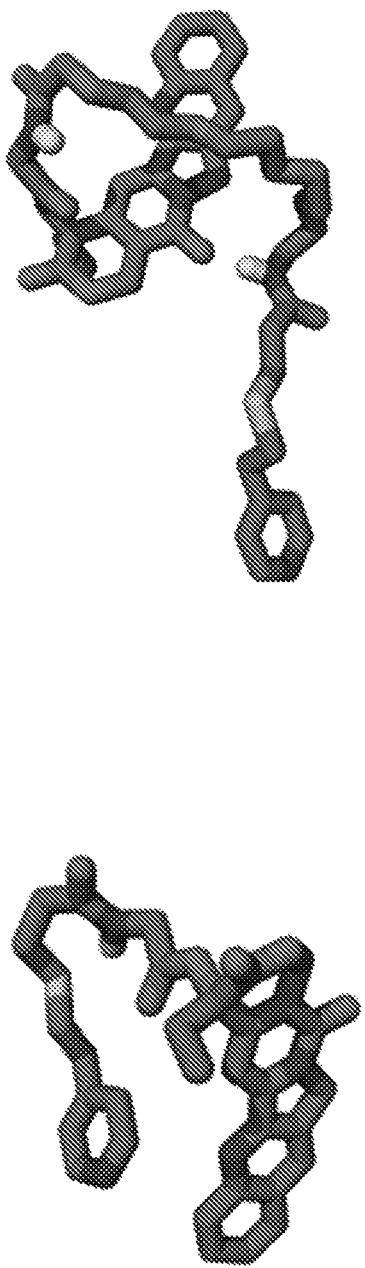
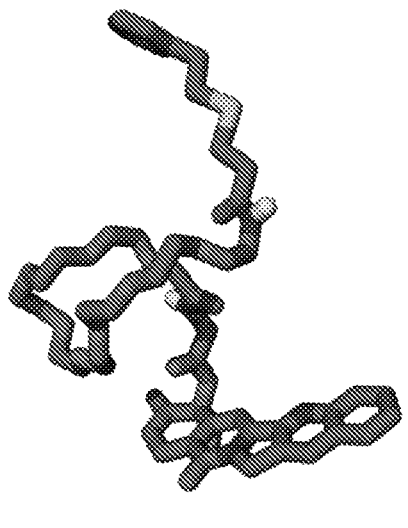
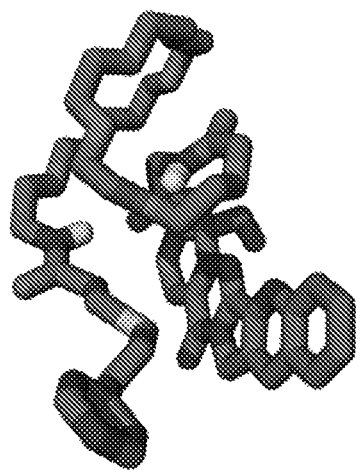
FIG. 10
1) IO-1009_01 (MEP+CPT)
2) IO-1017_01 (MEP+4PEG+CPT)
3) IO-1024_02 (MEP+8PEG+CPT) Closed conformation
4) IO-1024_02 (MEP+8PEG+CPT) Open Conformation

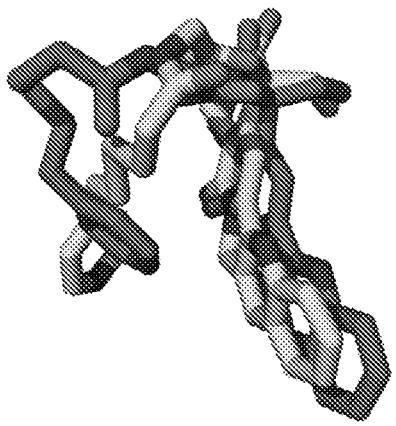
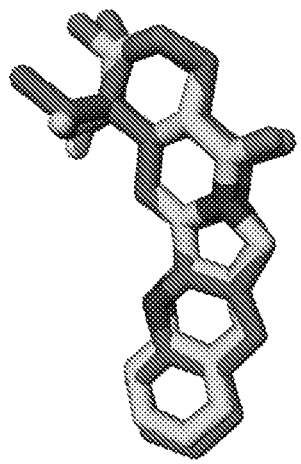
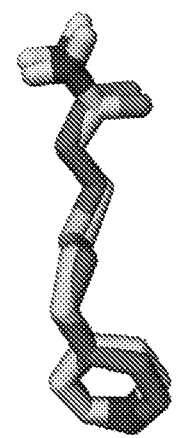
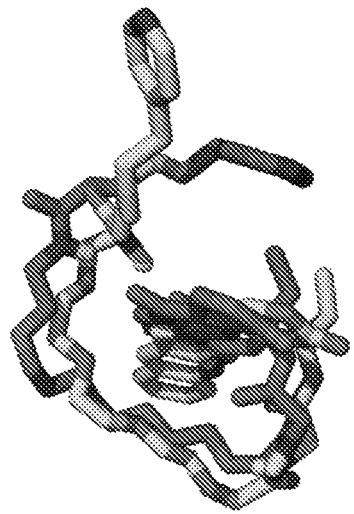
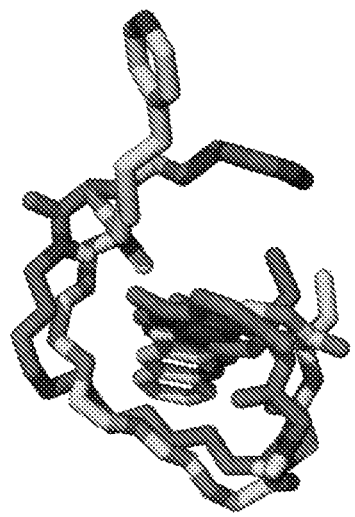
3) IO-1009_01 (MEP+CPT)
2) Camptothecin alone
1) MEP alone
5) IO-1024_02 (MEP+8PEG+CPT)
4) IO-1017_01 (MEP+4PEG+CPT)
FIG. 11

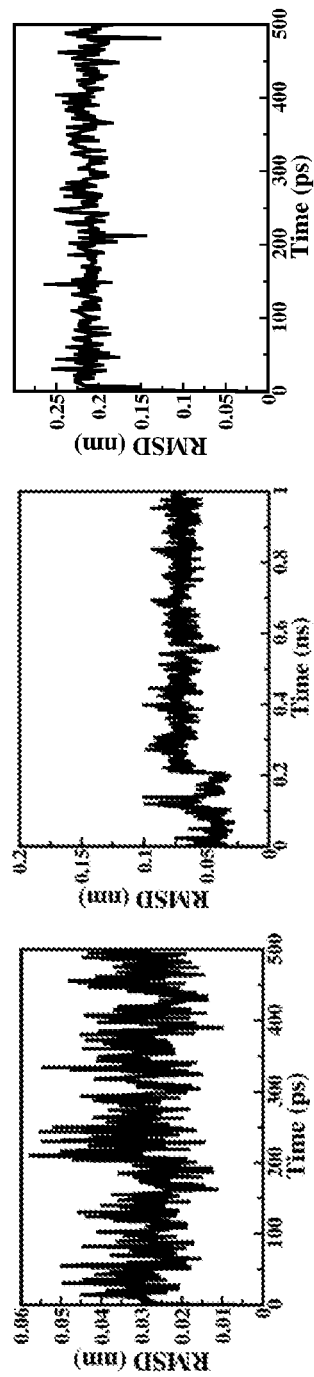
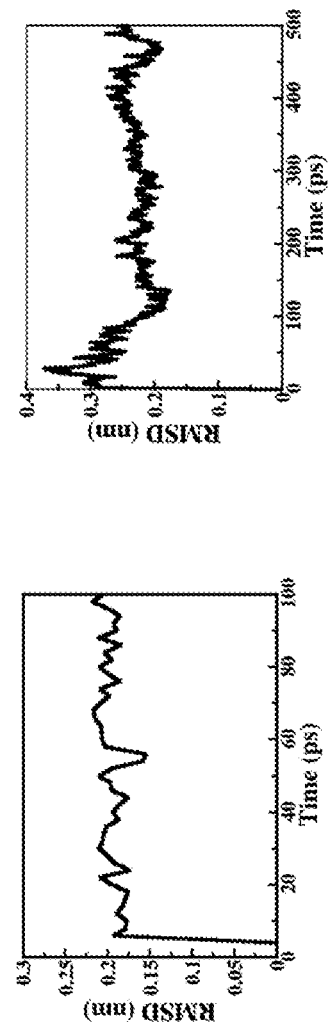
FIG. 12

EVALUATION AND OPTIMIZATION OF SUPRAMOLECULAR THERAPEUTICS

CROSS-REFERENCE TO RELATED APPLICATIONS

This application is a 371 National Phase Entry of International Application No. PCT/US2017/040699 filed on Jul. 5, 2017 which claims benefit under 35 U.S.C. § 119(e) of the U.S. Provisional Application No. 62/358,297, filed Jul. 5, 2016, the content of which is incorporated herein by reference in its entirety.

BACKGROUND

Nature has inspired the design of many engineered materials and devices (Wegst U G K, Bai H, Saiz E, Tomsia A P, Ritchi R O. Bioinspired structural materials. Nature Materials 14, 23-36 doi:10.1038/nmat4089 and Huebsch N, Mooney D. J. Inspiration and application in the evolution of biomaterials. *Nature* 462, 426-432 (26 Nov. 2009). For example, the nanotopography of gecko feet inspired the development of surgical adhesives (Mandavi et al., A biodegradable and biocompatible gecko-inspired tissue adhesive. Proc Natl Acad Sci USA. 2008; 105(7):2307-12). Similarly, a cephalopod's ability to display vivid colors by selectively contracting muscles to reversibly activate chromatophores recently inspired the development of an electro-mechano-chemically responsive elastomer system that can exhibit a wide variety of fluorescent patterns under the control of electric fields (Wang et al., Cephalopod-inspired design of electro-mechano-chemically responsive elastomers for on-demand fluorescent patterning. Nature Communications. 5, 4899. doi:10.1038/ncomms5899). In the evolution of organisms, an extensively studied system is the Volvocine family including the unicellular *Chlamydomonas* and the first multicellular organism, Volvox, where simplistically the latter is comprised of about 2000 somatic cells (and a few germ cells) that resemble *Chlamydomonas* cells routinely arranged in a self-assembling extracellular matrix (David L Kirk. Evolution of multicellularity in the volvocine algae. Current Opinion in Plant Biology 1999, 2. 496-501). The evolution from unicellularity to multicellularity confers complexity of function (David L Kirk. Evolution of multicellularity in the volvocine algae. Current Opinion in Plant Biology 1999, 2. 496-501). In the chemical world, such an evolution is mirrored in the origin of supramolecular structures from molecular subunits (Lehn J M. Toward complex matter: supramolecular chemistry and self-organization. Proc Natl Acad Sci USA. 2002 Apr. 16; 99(8):4763-8). We rationalized the complexity of function thus acquired in a supramolecular system over a molecular subunit could be potentially harnessed in the treatment of cancer and other inflammation-associated diseases.

According to the World Health Organization, mortality due to cancer is expected to increase from 7.6 million in 2008 to 12 million deaths in 2030, making it one of the major killers (Torre et al., Global cancer statistics, 2012. CA Cancer J Clin. 2015 Feb. 4. doi: 10.3322/caac.21262). While emerging approaches such as immunotherapy hold promise in the treatment of cancer, these produce durable response in only a fraction of the cancer patients (Kim et al., Combining targeted therapy and immune checkpoint inhibitors in the treatment of metastatic melanoma. Cancer Biol Med. 2014 December; 11(4):237-46). This necessitates a reliance on small molecule therapeutics or biologics, which are limited by the inability to achieve high concentrations in the tumor without causing systemic toxicity. While nanomedicines and antibody-drug conjugates address these limitations by delivering greater quantities of a therapeutic payload to a tumor, the ability to load enough payload onto the carrier to achieve the desired therapeutic concentrations is a challenge (Basu et al., Nanoparticle-mediated targeting of MAPK signaling predisposes tumor to chemotherapy. Proc Natl Acad Sci USA. 2009 May 12; 106(19):7957-61 and Sengupta S and Kulkarni A. Design principles for clinical efficacy of cancer nanomedicine: a look into the basics. ACS Nano. 2013 Apr. 23; 7(4):2878-82). Interestingly, this challenge can be overcome using supramolecular therapeutics, where molecular subunits self-assemble through supramolecular 'weak' interactions to form large complex structures (Lehn J M. Perspectives in Supramolecular Chemistry—From Molecular Recognition towards Molecular Information Processing and Self-Organization. Angewandte Chemie (Int. Ed.). 29, 1304-1319 (1990)). This evolution in dimensional complexity confers unique functional advantages over the molecular subunits in that they are restricted to systemic circulation, minimizing exposure to normal tissue, while homing into tumors through an EPR (enhanced permeability and retention) effect arising from leaky tumor vasculature (Maeda H, et al., Tumor vascular permeability and the EPR effect in macromolecular therapeutics: a review. J. Cont. Release. 65, 2000, 271-284). However, the current approaches of engineering supramolecular therapeutics rely on a stochastic design of molecular subunits, without much insight into their mechanisms of self-assembly or interactions with additional excipients, which pose a significant barrier to expanding the repertoire of supramolecular therapeutics.

SUMMARY

Described herein is a process for designing supramolecular therapeutics, based on a recursive integration of computational modeling and human thought process. This process is also referred to as Volvox herein. Generally, the process comprises sequential integration of quantum mechanical energy state- and force field-based models of molecules with large scale all atomistic explicit water molecular dynamic simulations of interactions with excipients, and human interpretation of the stability analytics to design optimal molecular structures that form stable supramolecular interactions. In one example, the process is used to design a taxane supramolecular therapeutic. In another example, the process is used to demonstrate the need to optimize the ratio of a pegylated polymer and a distinct molecular taxane subunit leading to the formation of a stable supramolecular therapeutic. In a third example, the process is used to convert a kinase inhibitor into a supramolecule. Thus, Volvox-inspired supramolecular therapeutics can emerge as an attractive strategy in the treatment of disease.

In another aspect, the disclosure provides a method for designing and/or optimizing antibody drug conjugates (ADCs).

BRIEF DESCRIPTION OF THE DRAWINGS

FIGS. 1A-1G show embodiments of using Volvox to design a supramolecular therapeutic. FIG. 1A, the algorithmic process used to design supramolecules. The simulation starts with a molecule that has a biological target, and may have a biological effect. Here we have used paclitaxel (FIG. 1C) as an example. Module 1 results in generating an energy-optimized simulated structure of the active agent. FIGS. 1C-1E show MD-optimized structures of paclitaxel, STX1 and STX2. The molecules are then packed with excipients using the steps outlined in module 2. The steps to achieve such large scale packing is shown in FIG. 1B. The MD-simulations are then run, and the trajectories are generated (analysis of stability is shown in FIGS. 2A-2G). FIG. 1F shows a typical trajectory obtained with 20 mol % PTX and a lipid (SOPC) shows ripple formation, which is a prediction that the resulting supramolecule will be unstable. In module 3, information from module 2 is used to design newer molecules using the starting chemical substrate (paclitaxel). STX1 was engineered by conjugating cholesterol to paclitaxel, and then looped through Module 1 and 2. However, as shown in FIGS. 3A-3F, STX1 does not improve the stability parameters. Based on this input, STX2 was designed, which included a flexible linker of defined length between the cholesterol tether and the taxane. STX2 forms a stable supramolecular structure (FIG. 1G).

FIGS. 2A-2G show exemplary analytics used to quantify the stability of a simulated paclitaxel-templated supramolecule. FIG. 2A is a schematic representation for tilt angle calculation. Tilt angle is the angle between vector joining centre of mass of phospholipid tails and Z-axis (axis perpendicular to bilayer plane). Value of tilt angle is positive or negative depending on direction of the ripple. Its value is close to 0° when no ripples form. FIG. 2B shows distribution of tilt angle averaged over last 5 ns of MD trajectory. Broader the distribution larger is the tilt angle, hence, higher is the extent of ripple formation. Wider distribution for PTX (red line) than STX (blue line) represents larger ripple formation for PTX compared to STX. Further, peak height of distribution at 0° is higher for STX than PTX. Thus, PTX is away from no ripple state more than STX. FIG. 2C is a schematic representation of angle (θ) between vector defined on C—C bond on SOPC tail with Z-axis (axis perpendicular to bilayer plane). Deuterium order parameter (Scd) is calculated using θ. Scd is calculated on each carbon atom of phospholipid tail. Higher the –Scd higher is the lipid tail ordering. FIG. 2D shows deuterium order parameter on each methylene group on saturated tail of SOPC is depicted. Lipid tail ordering for PTX containing SOPC bilayer is least. Tail ordering of STX containing SOPC bilayer is lower than pure SOPC but higher than PTX containing bilayer. FIG. 2E is a representation of unit volume inside the hydrophobic core of lipid bilayer where number of water molecules per unit volume is computed. Penetration of water molecules into the hydrophobic core of the bilayer is indicative of its instability. The hydrophobic region of the bilayer is divided into grids and number of water molecules falling in these grids was counted. Count in divided by volume of the grid to obtain number of water molecules per unit volume. FIG. 2F shows probability of finding water molecules per unit volume were calculated normalizing the count per unit volume with number of frames in last 5 ns of MD trajectory. More number of water molecules penetrates the PTX containing bilayer compared to STX containing bilayer. It indicates that PTX containing bilayer is less stable than STX containing bilayer. FIG. 2G shows cluster size of PTX/STX molecules in the lipid bilayer. It represents aggregation of PTX/STX molecules in the lipid bilayer. Higher peaks at larger cluster size for PTX compared to STX indicate more aggregation of PTX molecules in PTX containing bilayer.

FIGS. 3A and 3B show QM representation of structures of paclitaxel (PTX), STX1 and STX2. FIG. 3C shows that Volvox-based simulation shows STX1 forms ripples, and is no better than PTX in forming a supramolecular structure. FIG. 3D shows dDistribution of tilt angle averaged over last 5 ns of MD trajectory. Broader the distribution larger is the tilt angle, hence, higher is the extent of ripple formation. Wider distribution for PTX (red line) than STX (blue line) represents larger ripple formation for PTX or STX1 compared to STX2. Further, peak height of distribution at 0° is higher for STX2 than PTX or STX1. Thus, PTX or STX1 is away from no ripple state more than STX2. Lipid tail ordering for PTX and STX1 containing SOPC bilayer is least. Tail ordering of STX containing SOPC bilayer is lower than pure SOPC but higher than PTX containing bilayer. FIG. 3E shows the Scd. FIG. 3F shows the probability of finding water molecules per unit volume were calculated normalizing the count per unit volume with number of frames in last 5 ns of MD trajectory. More number of water molecules penetrates the PTX containing bilayer compared to STX containing bilayer. It indicates that PTX or STX1 containing bilayer is less stable than STX2 containing bilayer.

FIG. 4C shows that Volvox-based simulation shows both CBZ and SCBZ form ripples. FIG. 4D shows distribution of tilt angle averaged over last 5 ns of MD trajectory. Broader the distribution larger is the tilt angle, hence, higher is the extent of ripple formation. Similar distribution for CBZ (red line) and SCBZ (blue line) represents ripple formation in both systems. FIG. 4E shows that lipid tail ordering for CBZ and SCBZ are similar, as is the (FIG. 4F) Probability of finding water molecules per unit volume were calculated normalizing the count per unit volume with number of frames in last 5 ns of MD trajectory. To address this, increasing concentrations of PEG-DSPE200 was added. As shown in graphs (FIG. 4H-4J), the addition of the excipient can reduce tilt angle and entry of water and stabilize the system although lipid ordering remains unchanged.

FIGS. 5A-5F show that Volvox can be used to analyze the effect of minor structural differences in drugs on their ability to form stable supramolecular structures. FIGS. 5A and 5B show that Cabazitaxel and paclitaxel only vary at the above sites. FIG. 5C show QM representation of structures of cabazitaxel (cBZ) and a cholesterol-tethered cabazitaxel (SCBZ) engineered to act as a subunit for supramolecular assembly. FIG. 5D show packing of the SCBZ in lipid bilayer. FIGS. 5E and 5F show that CBZ can form more stable supramolecular assembly than PTX. FIG. 5F show that Volvox-based Simulations reveal that at low mol %, the molecular subunits can form stable structures.

FIG. 6 shows an exemplary use of Volvox to engineer a kinase-inhibiting supramolecule. Volvox predicted that the molecular subunit on top can form pi-pi interactions within a bilayer and form clusters that can precipitate out (inset). Based on this input a subunit (below) was engineered, which forms a stable supramoleular structure. Orange is the head group pf the lipids, while green is the molecular subunit. The resultant supramolecule can target PI3K signaling.

FIG. 10 shows the energetically favorable conformations of IO-1009_01, IO-1017_01 and IO-1024_02

FIG. 11 shows the overlap structures of QM optimized conformation with MD produced conformation.

FIG. 12 shows the RMSD values of ligands with developed force field.

(FIG. 15C), IO-107_01 (FIGS. 15D and 15E), IO-102_02 (Open conformation) (FIG. 1F) and IO-1024_02 (Closed Conformation) (FIG. 15G).

DETAILED DESCRIPTION

Figure 1F:
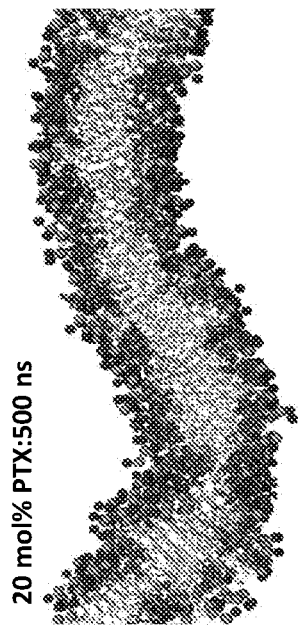

Described herein is method for evaluating and/or optimizing supramolecular therapeutics. This is a computation-human interaction-based platform technology, also referred to as Volvox herein, inspired by the evolution of multicellularity from self-assembly of unicellular building blocks, which can enable a rational high-throughput design of supramolecular therapeutics. The process is based on the sequential integration of quantum mechanical energy state- and force field-optimized molecular structures of subunits with large scale all atomistic explicit water molecular dynamic simulations to study the high-dimension interactions of the molecular subunits with lipid bilayers, and the manual introduction of modifications into the chemical template of the evolving subunit, cyclically iterating the process with such rationally modified subunits or altered excipients till a stable supramolecular interaction is predicted.

Generally, the process is set up as a three connected iterative-recursive modules (FIGS. 1A-1C). In the first module, a force field for the molecular subunit is prepared (FIG. 1A). Generally this comprises performing a geometry optimization of the subunits using quantum mechanical (QM) methods to obtain the lowest energy conformation of the molecular subunit. Following the QM optimization step, partial charges on each atom of the drug molecules are computed and electrostatic potentials are fitted. The partial charges can be calculated using, for example, Gaussian 09 with B3LYP exchange correlation functional and 6311G basis set. The electrostatic potentials can be fitted with, for example, with CHELPG scheme. Following fitting of electrostatic potentials, the force field parameters of the molecular subunit are calculated. For example, bond and angle potential parameters can be taken, for example, from CHARMM force field. Dihedral potentials can also be taken from CHARMM force field. Any dihedral potential that is not present in the CHARMM force field can be calculated and parameterized. In terms of non-bonded potentials, Lennard-Jones (LJ) parameters can be taken from CHARMM force field, while for coulomb potential, partial charges on each atom obtained from QM calculations can be used. Following the force field development step, the subunit was energy optimized using the developed force field. We next performed a short molecular dynamics (MD) simulation of the molecular subunit in vacuum using the developed force field, and the output structure obtained was matched with the structure obtained after QM optimization of the drug molecule. If the structures obtained did not match, we looped back to the force field development circle, and different parameters were tweaked, and this iteration continued till the structures obtained after QM optimization and MD in vacuum matched, at which stage it was advanced to the second module.

The second module of the process comprises modeling of supramolecular therapeutics involved an all atomistic molecular dynamics simulation of the QM-optimized matched structures of the molecular subunits packed with the excipient lipids (FIG. 1B). Atomistic simulations have indeed been used previously to investigate the fluidity and packing of pre-assembled lipid bilayers (Wataru et al., Molecular dynamics study of a lipid bilayer: Convergence, structure, and long-time dynamics. J. Chem. Phys. 106, 5731 (1997)). Due to their hydrophobic-hydrophilic structural arrangements, lipid bilayers are considered as good models of plasma membrane, and have also been used in atomistic simulations of drug permeating through lipid bilayers (Daniele Bemporad et al., Permeation of Small Molecules through a Lipid Bilayer: A Computer Simulation Study. *J. Phys. Chem. B*, 2004, 108 (15), pp 4875-4884). Recently, atomistic simulations were used in the understanding of the interactions of nanomaterials with cell membrane, such as the extraction of phospholipids by graphene sheets from membranes of *E. coli* (Tu, et al., Destructive extraction of phospholipids from *Escherichia coli* membranes by graphene nanosheets. Nature Nanotechnology 8, 594-601 (2013)) or the insertion and translocation of nanoparticles across cell membranes (Yang K and Ma Y. Computer simulation of the translocation of nanoparticles with different shapes across a lipid bilayer. Nature Nanotechnology 5, 579-583 (2010)). However, no studies have ever been done to understand the intermolecular interactions of large number of drug and drug-like molecules with excipients such as lipids.

Generally, the second module comprises constructing a large simulation cell, to pack the large scale structurally big molecular subunits, for example, a therapeutic agent. This can be carried using the steps shown in FIG. 1B. Briefly, the molecular subunits (two spherical particles representing the force fields as shown in FIG. 1B) are placed in a simulation cell parallel to z-axis (in case of lipid bilayer-water interfacial plane is perpendicular to z-axis), and are translated along x-axis (or y-axis) stepwise to first obtain a box containing N/4 and then N/2 subunits, wherein N is desired number of molecular subunits. Generally, translation is carried out such that the Z-coordinates do not vary within a predetermined limit and the particles are placed randomly in the XZ and YZ-planes. At each step, the energy can be minimized using steepest descent/conjugate gradient algorithm using the derived force field for the subunit. The configuration of the N/2 subunits is then solvated in an equilibrated box of lipid bilayer-water molecules at desired mole percent. Generally, this solvation is performed depending upon the van der Waals (vdw) radii of the different atoms present in the system, where any of the incoming lipid or water molecules falling within vdw radii of the particles present are removed. The box containing N/2 subunits is then energy minimized using steepest descent or conjugate gradient algorithm. A short molecular dynamics (MD) simulation step using isotropic pressure coupling is performed to allow the lipids and the subunits to pack, and remove any extra vacuum created inside the simulation box, and also to remove any water molecules that may have penetrated the hydrophobic core of lipid bilayer during the packing. Following these steps, the box containing N/2 subunits and M/2 lipid molecules is then further translated to construct a larger simulation cell with N subunits and M lipid molecules. This step creates a larger simulation cell, implying more number of building blocks, but keeping the mole percent of the molecular subunits in the lipid bilayer constant. The box containing N subunits, M lipid molecules and water was energy minimized using steepest descent or conjugate gradient algorithm, followed by a short MD step with isotropic pressure. If any water molecules are found to have penetrated the hydrophobic core of lipid bilayer during the packing, they are removed, and the previous step is repeated. Finally, MD simulation is performed with semi-isotropic pressure coupling, and trajectory is analyzed using parameters for stability.

Module 3 of the process represents the interface between computer-generated analytics and human decision-making. An upper bound of a stable supramolecular structure is set using the trajectory obtained with a pure lipid bilayer and lower bound is set using a trajectory obtained with a bilayer spiked with the template bioactive molecule. This template, which destabilizes a lipid bilayer, serves as the starting point to build the supramolecular structure. Minor modifications can be made to the subgroup based on human intelligence-based decisions, and the modified molecule looped through Module 1 and 2. The resultant trajectories are compared with the set bounds. If it is close to the upper bound, minor modifications can be made to test if it can be further improved. If it is above the lower bound but below the upper bound, then structural modifications are made ideally away from the active sites of the molecule. Such structural modifications can include, for example, adding a chemical tether directly or via a linker. If the trajectory is below or overlaps the lower bound, the process can be modified to include, for example, inserting additional excipients into the simulation. The selection of the right excipient or the chemical modifications to the chemical backbone/template can be based on human intelligence. Thus starting from the known bioactive molecular template, and tweaking the molecular structure iteratively based on inputs from the trajectory analysis, with the goal to achieve the bound set by the pure lipid bilayer, the recursive nature of the process provides a final molecular subunit configuration that can facilitate and increase formation of a supramolecular therapeutic. (FIGS. 1A-1E).

In an exemplary embodiment, the method for evaluating and/or optimizing a supramolecular therapeutic comprises the steps of: (a) calculating a quantum mechanics (QM) optimized matched structure for a subunit (therapeutic agent) of the supramolecular therapeutic; (b) calculating an all atomistic molecular dynamics simulation of said QM-optimized matched structure; (c) comparing trajectory of simulation cell from step (b) with an upper bound trajectory and a lower bound trajectory, wherein the upper bound trajectory is a trajectory obtained with a pure lipid bilayer and the lower bound trajectory is a trajectory obtained with a lipid bilayer with a nonoptimized structure for the therapeutic agent; and (d) modifying structure of the subunit and repeating steps (a)-(d) unless trajectory is substantially close to the upper bound trajectory.

Generally, the step calculating a quantum mechanics (QM) optimized matched structure for a subunit (therapeutic agent) of the supramolecular therapeutic comprises the steps: (i) optimizing geometry of said subunit using quantum mechanical methods; (ii) calculating a plurality of force field parameters from the optimized subunit of step (i); (iii) optimizing energy of the subunit using the plurality of force field parameters calculated in step (ii); (iv) optimizing geometry of the subunit of step (iii) via molecular dynamics (MD) simulation of said subunit in vacuum using the plurality of force field parameters calculated in step (ii); and (v) comparing the optimized subunit of step (i) with the optimized subunit of step (iii), wherein, if the optimized subunits differ from each other, changing at least one of the plurality of force field parameters calculated in step (ii) and repeating steps (ii)-(v).

Generally, the step of calculating an all atomistic molecular dynamics simulation of said QM-optimized matched structure comprises the steps: (i) forming a simulation cell by placing two of the said QM-optimized matched structures in a simulation cell parallel to z-axis of said simulation cell; (ii) translating the said QM-optimized matched structures along x-axis of the simulation cell, thereby doubling a number of QM-optimized matched structure in the simulation cell; (iii) optimizing energy of the simulation cell using a steepest descent/conjugate gradient method; (iv) translating the QM-optimized matched structures in the simulation cell of step (iii) along the x-axis, thereby doubling the number of QM-optimized matched structures in the simulation cell; (v) repeating steps (iii)-(iv) until number of QM-optimized matched structures in the simulation cell is half of a predetermined number N; (vi) solvating the QM-optimized matched structures with an equilibrated box of lipid bilayer and water molecules, wherein number of lipid molecules in the lipid bilayer is half of a predetermined number M of lipid molecules; (vii) minimizing energy of the simulation cell from step (vi) using a steepest descent/conjugate gradient method; (viii) packing the lipids and the QM-optimized matched structures by molecular dynamics simulation of the simulation cell of step (vii) with isotropic pressure coupling; (ix) removing any additional empty spaces created inside the simulation cell; (x) removing any water molecules from hydrophobic core of lipid bilayer; (xi) translating the simulation cell of (x) to form a large simulation cell comprising N QM-optimized matched structures and M lipid molecules; (xii) minimizing energy of the large simulation cell of (xi) using a steepest descent/conjugate gradient method; (xiii) packing the large simulation cell of (xiv) using a molecular dynamics simulation with isotropic pressure coupling; (xv) removing any water molecules from hydrophobic core of lipid bilayer; and (xvi) packing the simulation cell of (xv) using a molecular dynamics simulation with semi-isotropic pressure coupling

EXAMPLES

Example 1: Designing a Volvox-Inspired Taxane Supramolecular Subunit

We set a high bar to test the applicability of Volvox in the development of a stable supramolecular therapeutic. We selected taxanes, which are one of the most widely used anticancer drugs (Bedard et al., Taxanes: optimizing adjuvant chemotherapy for early-stage breast cancer. *Nature reviews. Clinical oncology* 7, 22-36, doi:10.1038/nrclinonc.2009.186 (2010)) but are notorious for precipitating out of lipid bilayers, as the template to engineer a supramolecule. The hydrophobic, asymmetric, non-flexible structure of a typical taxane molecule such as paclitaxel (PTX), a diterpenoid centered around a bulky and fused taxane ring with multiple hydrophobic substitutions, (FIG. 1C) has meant that entrapping of taxanes in lipid-based nanoparticles have remained a holy grail even after two decades of research (Koudelka, S. & Turanek, J. Liposomal paclitaxel formulations. *Journal of controlled release: official journal of the Controlled Release Society* 163, 322-334, doi: 10.1016/j.jconrel.2012.09.006 (2012)). We rationalized that a taxane supramolecule, where the taxane subunits are designed to assemble into supramolecular structures, could overcome the current limitations of taxane chemotherapy (Bedard et al., Taxanes: optimizing adjuvant chemotherapy for early-stage breast cancer. *Nature reviews. Clinical oncology* 7, 22-36, doi:10.1038/nrclinonc.2009.186 (2010)).

Figure 3A:
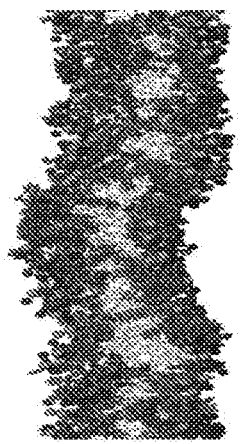
FIGS. 3A-3F show exemplary analytics used to quantify the stability of a simulated supramolecule show that recursive loop and human intelligent design of structure improves the stability of supramolecules.

As the first step towards developing a taxane supramolecule, we used Volvox to build a model of dynamic interactions of PTX with a lipid bilayer. Structures obtained after QM optimization and short MD in vacuum for paclitaxel are shown in FIGS. 1D and 3A. Simulations were performed at a low (5%) and high (20%) mol concentration of PTX incorporated in a bilayer system made of 1-octadecanoyl-2-(9Z-octadecenoyl)-sn-glycero-3-phosphocholine (SOPC), where the force field parameters for SOPC were adapted from an atomistic CHARMM-based (Klauda, J. B. et al. Update of the CHARMM all-atom additive force field for lipids: validation on six lipid types. *The journal of physical chemistry. B* 114, 7830-7843, doi:10.1021/jp101759q (2010)) force field proposed for phosphatidylcholine lipids (Jambeck, J. P. & Lyubartsev, A. P. Derivation and systematic validation of a refined all-atom force field for phosphatidylcholine lipids. *The Journal of physical chemistry. B* 116, 3164-3179, doi:10.1021/jp212503e (2012) and Jambeck, J. P. M. & Lyubartsev, A. P. An Extension and further Validation of an all-atomistic force field for biological membranes. *J. Chem. Theory Comput* 8, 11, doi:doi: 10.1021/ct300342n (2012)), and using a TIP3P water model (Jorgensen et al., Comparison of simple potential functions for simulating liquid water. *J. Chem. Phys.,* 79, 10, doi:doi: 10.1063/1.445869 (1983)). Models were constructed such that at the high taxane concentration (20 mol %), the system contained 256 molecules of SOPC and 64 molecules of geometry-optimized structure of PTX, while the low taxane (5 mol %) concentration setting contained 128 molecules of SOPC and 7 molecules of PTX. Interestingly, the unbiased atomistic simulations revealed that the lower concentrations of PTX led to stable interactions (but translationally not viable as therapeutic dose levels are difficult to achieve). However, higher concentration of PTX causes formation of large ripples in the bilayer structure in a very small length scale (FIG. 1F). The two ripples were periodic in nature (as we used a periodic boundary condition for our simulations), of length ~10 nm each in the bilayer throughout the simulation time of 500 ns, consistent with ripple formations associated with pre-transition between fluid and gel phases (Riske et al., Lipid bilayer pre-transition as the beginning of the melting process. *Biochimica et Biophysica Acta,* 1788, 10, doi: 10.1016/j.bbamem.2009.01.007 (2009) and Kranenburg, M. & Smit, B. Phase behavior of model lipid bilayers. *The Journal of physical chemistry. B* 109, 6553-6563, doi: 10.1021/jp0457646 (2005)), reflecting the strain caused by taxane molecules. Intriguingly, highly mobile fluidic domains mainly composed of PTX molecules and mostly oriented near the lipid head group and water interface were also observed (FIG. 1F). Formation of such large fluidic domains has been reported to increase the bilayer instability, hindering the formation of a stable supramolecular structure (Koudelka, S. & Turanek, J. Liposomal paclitaxel formulations. *Journal of controlled release: official journal of the Controlled Release Society* 163, 322-334, doi:10.1016/j.jconrel.2012.09.006 (2012)).

Figure 1G:
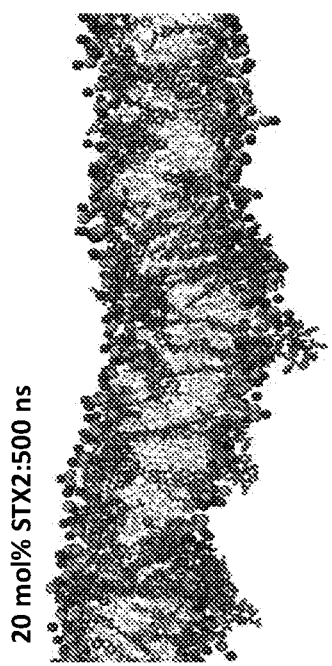
Figure 3B:
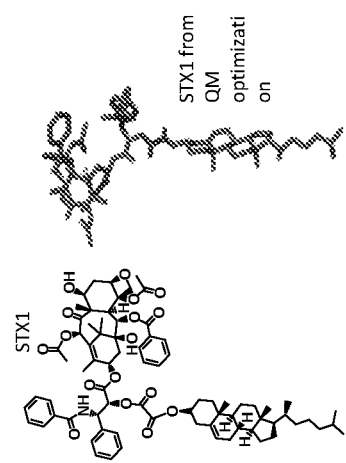
Figure 3C:
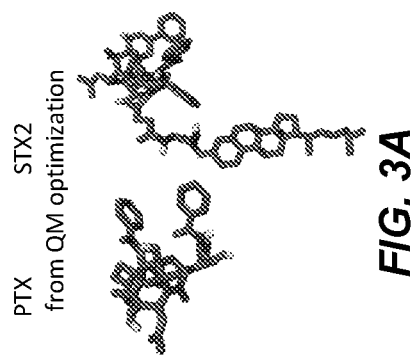
Figure 3D:
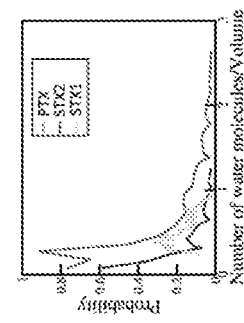
Figure 3E:
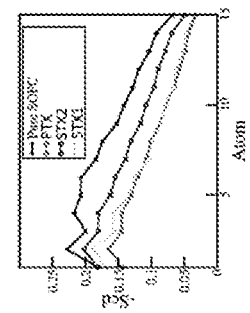
Figure 3F:
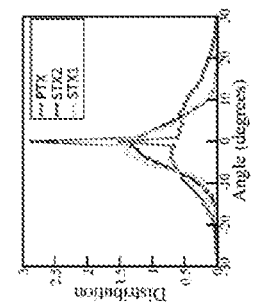

Based on this in silico trajectory analysis, we rationalized that to facilitate a supramolecular assembly, we needed to endow the taxane with a hydrophobic tail that could insert into the bilayer, reduce lipid mobility, while orienting the active taxane moiety towards the bilayer-water interface. Interestingly, this strategy was counter-intuitive to approaches that have been traditionally used for formulating taxanes, where the goal has been to synthesize more hydrophilic derivatives (Skwarczynski, M., Hayashi, Y. & Kiso, Y. Paclitaxel prodrugs: toward smarter delivery of anticancer agents. *Journal of medicinal chemistry* 49, 7253-7269, doi: 10.1021/jm0602155 (2006) and Dosio et al. Macromolecules as taxane delivery systems. *Expert opinion on drug delivery* 8, 33-55, doi:10.1517/17425247.2011.541437 (2011)). The presence of cholesterol in bilayer has been reported to affect the bilayer property by decreasing its free volume, increasing lipid tail order and packing and reducing the lipid mobility (Falck et al., Lessons of slicing membranes: interplay of packing, free area, and lateral diffusion in phospholipid/cholesterol bilayers. *Biophysical journal* 87, 1076-1091, doi:10.1529/biophysj.104.041368 (2004)). Indeed, atomic force microscopy (AFM) studies have shown that the incorporation of cholesterol molecules in phosphatidylcholine bilayer increases the Young's modulus and bending modulus of bilayers (Liang, X., Mao, G. & Ng, K. Y. Mechanical properties and stability measurement of cholesterol-containing liposome on mica by atomic force microscopy. *Journal of colloid and interface science* 278, 53-62, doi:10.1016/j.jcis.2004.05.042 (2004)). We therefore chose cholesterol as the tether to derivatize the taxane moiety. Previous structure activity relationship (SAR) studies with PTX have shown that C-2' OH group on the isoserine moiety of the C-13 side chain is important for its cytotoxic activity, and can be selectively conjugated without protecting C-7 OH group on the baccatin core due to large difference in reactivity (Fu, Y. et al. Medicinal chemistry of paclitaxel and its analogues. *Current medicinal chemistry* 16, 3966-3985 (2009)). We therefore designed a novel taxane subunit, which we term Suprataxel-1 (STX1), generated by conjugating cholesterol to C-2' position of PTX, which was then modeled using Volvox. The predicted structure of the STX1 is shown in FIGS. 1E and 3B. Partial charges of individual atoms in STX1 were computed as described earlier for PTX, using parameters (apart from charges) provided by Jambeck and Lyubartsev for the cholesterol part. The all atomistic MD simulations indicated only marginally increased stability of the supramolecular assembly as compared with PTX (FIG. 3C). We therefore next iterated whether the introduction of a flexible linker, 4-((2-aminoethyl)amino)-4-oxobutanoic acid of moderate length (~1 nm), between the taxane and the cholesterol moieties, chosen based on the criteria that it should not cause any structural changes in the taxane, and keep the orientation of the taxane near head group-water interface but provide the optimal insertion within the bilayer, could further stabilize the supramolecular assembly. The new Suprataxel analogue (STX2) (FIGS. 111 and 3A) was then subjected to Volvox analysis. Indeed, running STX2-bilayer MD simulations at 20 mol percent of STX2 molecules in SOPC bilayer for 500 ns using similar conditions as described earlier revealed a bilayer with significantly increased stability (FIG. 1G).

To quantify the degree of stability of the supramolecular bilayer, we measured the degree of ripple formation by calculating the angle between vector joining the center of mass of lipid tails and phosphorus (P) atom on the head group of SOPC molecule with z-axis (bilayer normal), where greater the angle, higher is the degree of instability (FIG. 2A). These angles were calculated and averaged along x-axis (perpendicular to bilayer axis) by dividing the simulation cell into 20 equal slabs. As compared to PTX, STX2 exhibited reduced ripple formation (FIG. 2B). Furthermore, the cholesterol moieties were arranged in the hydrophobic region of the bilayer directing the taxane component towards the head group-water interface for both 5 and 20 mol percent STX2. Therefore to identify the increase in magnitude of ordering of lipid tails in presence of STX2 and compare it with PTX, we calculated deuterium order parameter ($-S_{CD}$) for the SOPC lipid saturated tail from last 5 ns of the trajectory (Vermeer, L. S., de Groot, B. L., Reat, V., Milon, A. & Czaplicki, J. et al., Acyl chain order parameter profiles in phospholipid bilayers: computation from molecular dynamics simulations and comparison with 2H NMR experiments. *European biophysics journal: EBJ* 36, 919-931, doi:10.1007/s00249-007-0192-9 (2007)) (FIG. 2C). As shown in FIG. 2D, at both low and high mol %, PTX was found to decrease the ordering of the aliphatic tail groups by 30% compared to STX2. It should however be noted that the presence of large PTX moiety in STX did decrease the lipid tail ordering to certain degree compared to cholesterol alone.

The formation of ripples, and decrease in lipid tail order can result in perforations in the bilayer. Water molecules penetrate till the starting of hydrophobic region in lipid bilayer-water system (Pandey, P. R. & Roy, S. Headgroup mediated water insertion into the DPPC bilayer: a molecular dynamics study. *The journal of physical chemistry*. B 115, 3155-3163, doi:10.1021/jp1090203 (2011)). Interaction of lipid bilayer with external molecules may form water/ion channel through the bilayer (Choudhury, C. K., Kumar, A. & Roy, S. Characterization of conformation and interaction of gene delivery vector polyethylenimine with phospholipid bilayer at different protonation state. *Biomacromolecules* 14, 3759-3768, doi:10.1021/bm4011408 (2013)). To compare the permeability of the PTX- and STX-membrane systems, we calculated the probability of finding water molecules in per unit volume of hydrophobic region of the bilayer (FIG. 2E), which revealed that higher concentration of PTX increases the probability while the presence of STX2 hinders the permeation of water into the supramolecular structure (FIG. 2*f*). Thus the computationally-designed STX2 supramolecules show less perforation and have potential to form stable supramolecular assemblies at higher taxane concentration. We next calculated the probability of formation of aggregates of PTX and STX2 molecules in lipid bilayer in 20 mol percent systems. We had previously described that PTX has high tendency to aggregate in lipid bilayer at high concentration, probably arising from partial phase separation of lipid and PTX, which can make the bilayer unstable (Koudelka, S. & Turanek, J. Liposomal paclitaxel formulations. *Journal of controlled release: official journal of the Controlled Release Society* 163, 322-334, doi:10.1016/j.jconrel.2012.09.006 (2012)). Size of clusters formed by PTX or STX2 was calculated by searching neighbors within a cutoff of 2 nm (distance between center of masses), and represented as distribution of cluster size from last 5 ns trajectory. As shown in FIG. 2G, PTX molecules aggregated in larger size clusters compared to STX2 within the 20 mol % bilayer systems. Furthermore, studying the tilt angle and number of PTX molecules present in the same slab plotted as function of slab number in x-axis, revealed that the count of PTX molecules are more in particular slabs where the ripple appear, suggesting that aggregation of PTX can trigger ripple formation and hence instability, which can translate to a rapid release of the drug. On the contrary presence of flexible hydrophobic tail in STX2 decreased this aggregation by pinning the taxane moiety in the interface region. Interestingly, STX1 performed poorly compared with STX2 on all these parameter, and was closer to PTX in performance (data not shown). These results indicate that Volvox can emerge as a powerful tool in the design of subunits that underpin supramolecular therapeutics.

Example 2: Volvox Predicts Optimization of Excipients for Supramolecular Assembly We next evaluated whether the Volvox-based structural insights for engineering a supramolecular therapeutic using paclitaxel as the starting template for the subunit design were portable to a different molecule of the taxane family. We selected cabazitaxel, a recently approved taxane that differs from paclitaxel only by two methoxygroups and a tert-butyl carbamate ester that exists on the phenylpropionate side chain instead of the benzyl amide in paclitaxel (Bouchet B P & Galmarini C M. Cabazitaxel, a new taxane with favorable properties. Drugs Today (Barc). 2010 October; 46(10):735-42) (FIGS. 5A and 5B). We next generated a supramolecular subunit (SCBZ) starting with cabazitaxel as the template, conjugating C-2' OH group to cholesterol via the flexible 4-((2-aminoethyl) amino)-4-oxobutanoic acid linker. The structures of cabazitaxel or SCBZ obtained after QM optimization and MD in vacuum are shown in FIGS. 4A, 4B and 5C. The MD simulation using Volvox was set up as described previously (FIG. 5D). A comparison of the MD-simulation of CBZ and PTX interactions with SOPC bilayer revealed that PTX destabilizes the lipid bilayer to a greater degree as evident in the increased propensity to form ripples and decreased lipid tail order (FIG. 5E). Both CBZ and SCBZ formed stable supramolecular interactions at 5 mol % (FIG. 5F). Interestingly, the trajectories obtained from the Volvox-based simulations indicated that both cabazitaxel and SCBZ at 20 mol % resulted in unstable supramolecular structures (FIG. 4C), indicating that a direct transposition of a tether from one molecule to another may not suffice for supramolecular assembly. Indeed, plotting the angle between vector joining the center of mass of lipid tails and phosphorus (P) atom on the head group of SOPC molecule with z-axis (bilayer normal), revealed similar degree of ripple formation between CBZ and SCBZ (FIG. 4D). Additionally, the decrease in lipid tail order was comparable with both CBZ and SCBZ (FIG. 4E). Furthermore, while SCBZ did not decrease the probability of higher number of water molecules in the bilayer as compared with CBZ (FIG. 4F).

Figure 4A:
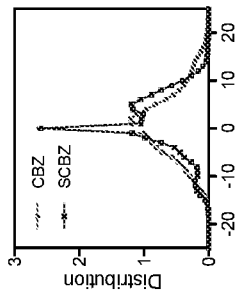
FIGS. 4A-4J shows Volvox-based design of a cabazitaxel-templated supramolecule. MD representation of structures of (FIG. 4A) cabazitaxel (cBZ) and (FIG. 4B) a cholesterol-tethered cabazitaxel (SCBZ) engineered to act as a subunit for supramolecular assembly.
Figure 4C:
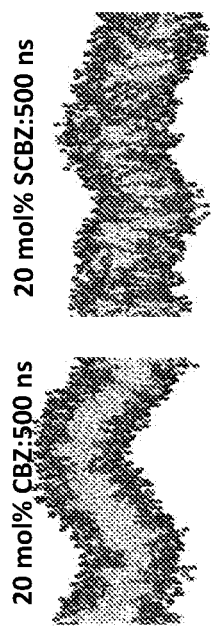
Figure 4B:
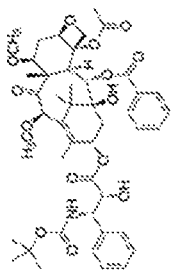
Figure 4D:
Figure 4F:
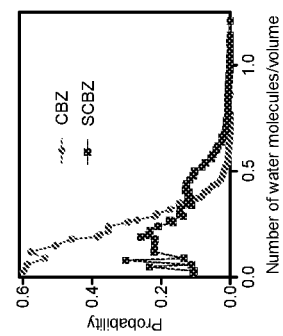
Figure 4E:
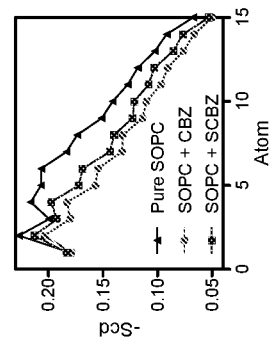
Figure 4G:
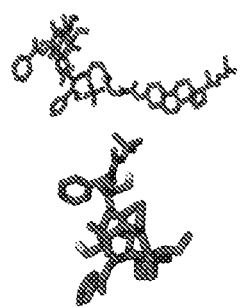
Figure 4J:
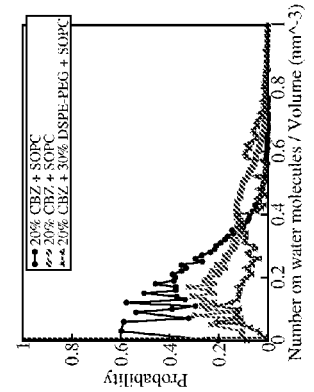
Figure 4I:
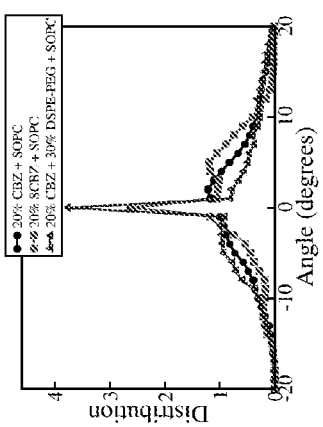
Figure 4H:
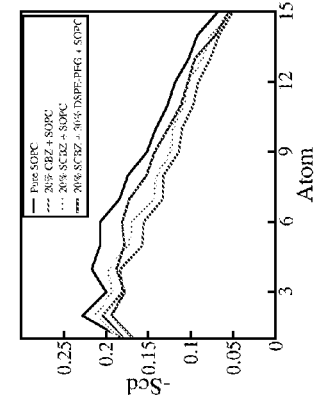
Figure 5F:
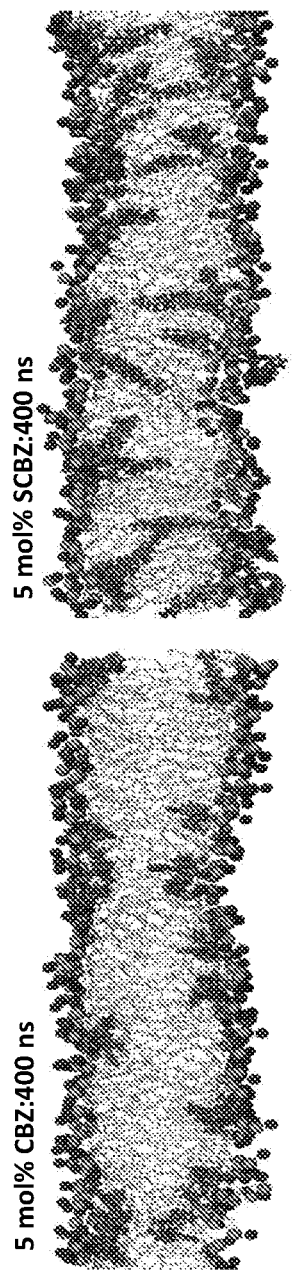
Figure 7:
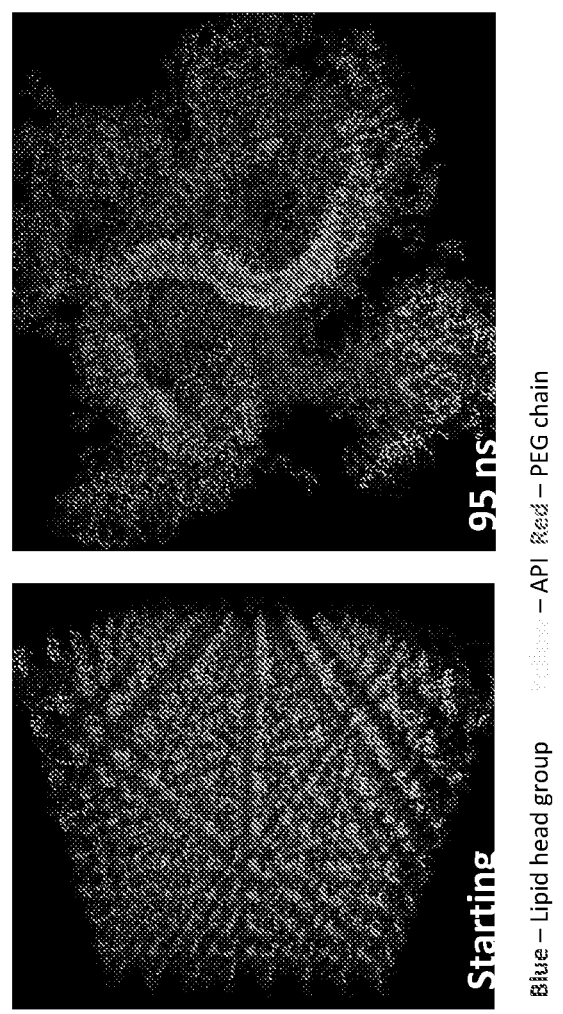
FIG. 7 shows use of coarse grain modeling to predict the interactions. Volvox can potentially use a coarse-grain-based simulation in module 2. Here a stable bilayer is seen forming at 20% API+5% DSPE-PEG+75% SOPC.

We next studied whether PEG-DSPE as an excipient could stabilize the SCBZ supramolecules. MD-simulations using the Volvox platform were run adding PEG2000-DSPE as an excipient (FIG. 4G). As shown in FIG. 4H, the addition of PEG-DSPE at 30 mol % did not affect the lipid tail ordering. However, we did observe a reduction in the ripple formation (FIGS. 4G and 4I) and a reduction in the entry of the water molecules in the lipid bilayer (FIG. 4J), indicating that the addition of PEG-DSPE could indeed stabilize the supramolecules.

Example 3: Using Volvox to Design a Kinase-Inhibiting Supramolecule

As shown in FIG. 6, Volvox was used to predict that the molecular subunit, PI103, a molecule that inhibits Pi3K signaling, on top can form pi-pi interactions within a bilayer and form clusters that can precipitate out (inset). Based on this input a subunit (below) was engineered, which forms a stable supramoleular structure.

The integration of all atomistic modeling into the design of supramolecular therapeutics has several translational implications. While we show an increased efficacy and improved systemic toxicity profile with paclitaxel supramolecules, the application of Volvox to design molecular subunits as well as optimize the excipients expands the repertoire of molecules that can be adapted into the supramolecular platform. Additionally, the modularity in the fabrication of supramolecules indicates that it may be possible to integrate biologics, such as the targeting peptide iRGD in the current study, or enable combination chemotherapy that can further enhance efficacy. The Volvox platform technology can thus emerge as a powerful tool in the search for an optimal cancer therapy.

Computational simulations: All the MD simulations were performed using GROMACS-4.6.1 package. All covalent bonds in SOPC, and PTX or STX were constrained with LINCS algorithm. SETTLE method was used to constrain the covalent bonds in water. Time step of 2 fs was used for all the simulations. Isothermal and isobaric ensemble (NPT) and periodic boundary condition (PBC) were used. Temperature was kept constant at 300 K for all the systems using Nose-Hoover thermostat with a coupling constant of 0.5 ps. Pressure was kept constant at 1 atm using Parrinello-Rahman barostat with coupling constant of 10 ps. Semi-isotropic pressure coupling was used. Neighbor searching was done with Verlet algorithm as implemented in Gromacs 4.6.1. For long range electrostatic interactions we have used particle mesh Ewald (PME) scheme with real space cut off of 1.4 nm. For van der Waals interactions 1.5 nm cut off was applied with a switching function at 1.4 nm. PTX or STX molecules were inserted inside the lipid bilayer structure and equilibrated till 10 ns for all the systems. After this trajectories were saved for further analysis.

Example 4: Design and Development of Antibody Drug Conjugates (ADCs)

Figure 8:
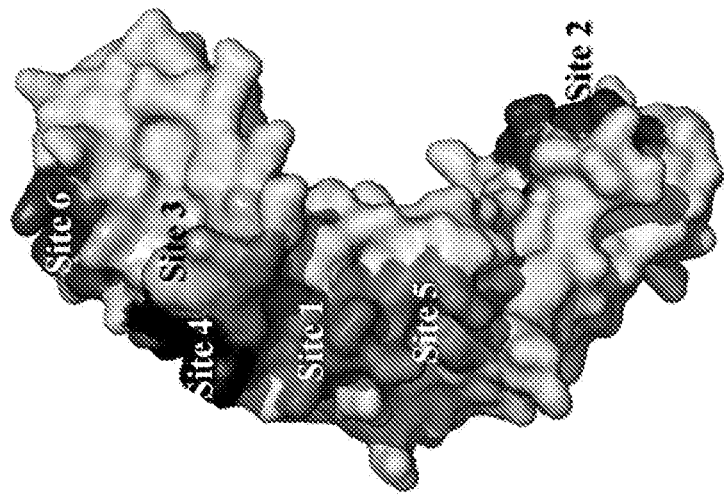
FIG. 8 shows the reported MEP binding bites on 1FC1 fragment.

Computational studies were performed on different IO (InvictusOncology) compounds for the design and development of ADC (Antibody Drug Conjugates) in the treatment of cancer. The development of novel ADC compounds with significant activity against the cancer is a subject of great interest to overcome the existing problems in the cancer therapy. Among these Specificity is one of the major issues, that the treated drug need to reach the cancer cell to show its proper mechanism of action and also it has to differentiate the cancerous cells with the normal cells to minimize the killing effect of the normal cells. In order to overcome these problems we need to focus mainly on increases in the specificity and availability of drugs for the targeted cancer cells. This helps us to decrease the off target and other side effects produced by the drugs for the better treatment of cancer. The Molecular interactions and affinity relationship of different IO compounds with the currently used effective anti-cancer antibodies were investigated. From the literature review, we came to know that 4-MEP (4-Mercaptoethyl-pyridine) was used as an alternative to protein A for the separation of IgG antibodies from a pool of various antibodies (Ghose, S., Hubbard, B. & Cramer, S. M. Evaluation and comparison of alternatives to Protein A chromatography Mimetic and hydrophobic charge induction chromatographic stationary phases. *J. Chromatogr. A* 1122, 144-52 (2006)). The pH based HCIC (hydrophobic charge induction chromatography) methods with MEP substrates was effectively used for the separation and elution of these IgG antibodies. At neutral pH, the MEP pyridine ring nitrogen exists with a neutral charge and can able to bind effectively with the hydrophobic pockets of the IgG Fc fragment. At lower pH, the nitrogen on the pyridine ring gets protonated and giving a positive electrostatic interaction with the antibody. These dominated positive electrostatic interactions cause the MEP unbinding and eluting the antibody at lower pH (Lin, D., Tong, H., Wang, H. & Yao, S. Molecular Insight into the Ligand-IgG Interactions for 4-Mercaptoethyl-pyridine Based Hydrophobic Charge-Induction Chromatography. *J. Phys. Chem. B* 116, 1393-1400 (2012)). These pH dependent MEP linkers plays an important role for the development of ADC compounds, such a way that it can able to release itself from the antibody in the micro environment of cancer cells, which were found to be in acidic condition compared with the normal cells (Gatenby, R. A. & Gillies, R. J. Why do cancers have high aerobic glycolysis? *Nat. Rev. Cancer* 4, 891-9 (2004)). Based on this concept we designed some new compounds by conjugating the potent anti-cancer drugs with MEP either directly (MEP-XXX) or through a spacer linker (MEP-LNK-XXX) that connects MEP with the potent drug (XXX). In the present study, we considered camptothecin (CPT) as a drug of choice for the preliminary development of ADC compounds. Cetuximab and trastuzumab antibodies were selected as a target for the preparation of ADC complexes. Cetuximab is a chimeric antibody, and trastuzumab is a humanized antibody (Scott, A. M., Wolchok, J. D. & Old, L. J. Antibody therapy of cancer. *Nat. Rev. Cancer* 12, 278-87 (2012)). Both antibodies share a common feature of IgG Fc fragment where the MEP substrates are able to show their binding. The cetuximab and trastuzumab are specific to EGFR receptors and HER2 receptors (Scott, A. M., Wolchok, J. D. & Old, L. J. Antibody therapy of cancer. *Nat. Rev. Cancer* 12, 278-87 (2012)) respectively, which helps us to increase the specificity of the target cancer cells by preparing ADC complexes with these antibodies. Thus we can enhance the cancer treatment with these ADC compounds to get better survival rates in the cancer patients. Six possible binding sites were reported by Lin et al. (Lin, D., Tong, H., Wang, H. & Yao, S. Molecular Insight into the Ligand-IgG Interactions for 4-Mercaptoethyl-pyridine Based Hydrophobic Charge-Induction Chromatography. *J. Phys. Chem. B* 116, 1393-1400 (2012)) on the IgG Fc fragment and site 1 was found to be energetically favorable for this MEP binding. The binding sites of Fc fragment are shown in FIG. 8 and their respective active site residues are reported in Table 1.

TABLE 1

The reported MEP Binding Sites and active site residues on 1FC1 fragment

| Sites | Residues |
|---|---|
| Site1 | VAL279, VAL284, ALA287, LEU306, VAL308, LEU309, ASN312, LYS317, TRY319 |
| Site2 | GLN362, GLU388, ASN389, ASN390, LEU410, VAL412, ASP413, ARG416 |
| Site3 | LYS274, PHE275, ASN276, GLN283, HIS285, ASN286, THR289, PRO291 |
| Site4 | TRY278, GLY281, VAL282, GLN283, GLU318, LYS320 |
| Site5 | THR250, LEU251, ILE253, HIS310, GLN311, HIS435 |
| Site6 | SER324, ASN325, LYS326, ALA327, LEU328, PRO329, PRO331 |

Materials and Methods

The following computational techniques were used.
1. BLAST—Used for the Sequence search analysis of protein for the selection of template
2. QM for optimization of ligand—To obtain lowest energy conformation of ligand and to calculate force field parameters to perform molecular dynamics simulations
3. Docking—To obtain starting conformations of the protein ligand complex
4. Molecular dynamic simulations—To study protein and ligand interactions
5. Umbrella sampling simulations—To compute the binding free energies of different ADC compounds The molecular docking studies and MD simulations are very effective to evaluate the molecular interactions between the protein and ligand complex systems.

Sequence Analysis:

The Cetuximab is a chimeric IgG antibody. The crystal structure of the cetuximab Fc fragment was not available. So that we performed a BLAST (Nucleic Acids Res. 25:3389-3402) sequence search by taking the Cetuximab Fc fragment sequence to select suitable template for our studies. The molecular structure of the Fc fragment of IgG with PDB ID 1FC1 (J. Biochemistry 1981, 20, 2361-2370.) was obtained from the Protein Data Bank (PDB). 1FC1 consists of two chains of A and B with CH2-CH3 constant domains of IgG1, which are identical in the amino acid sequence and are similar in the 3D structure.

Figure 9:
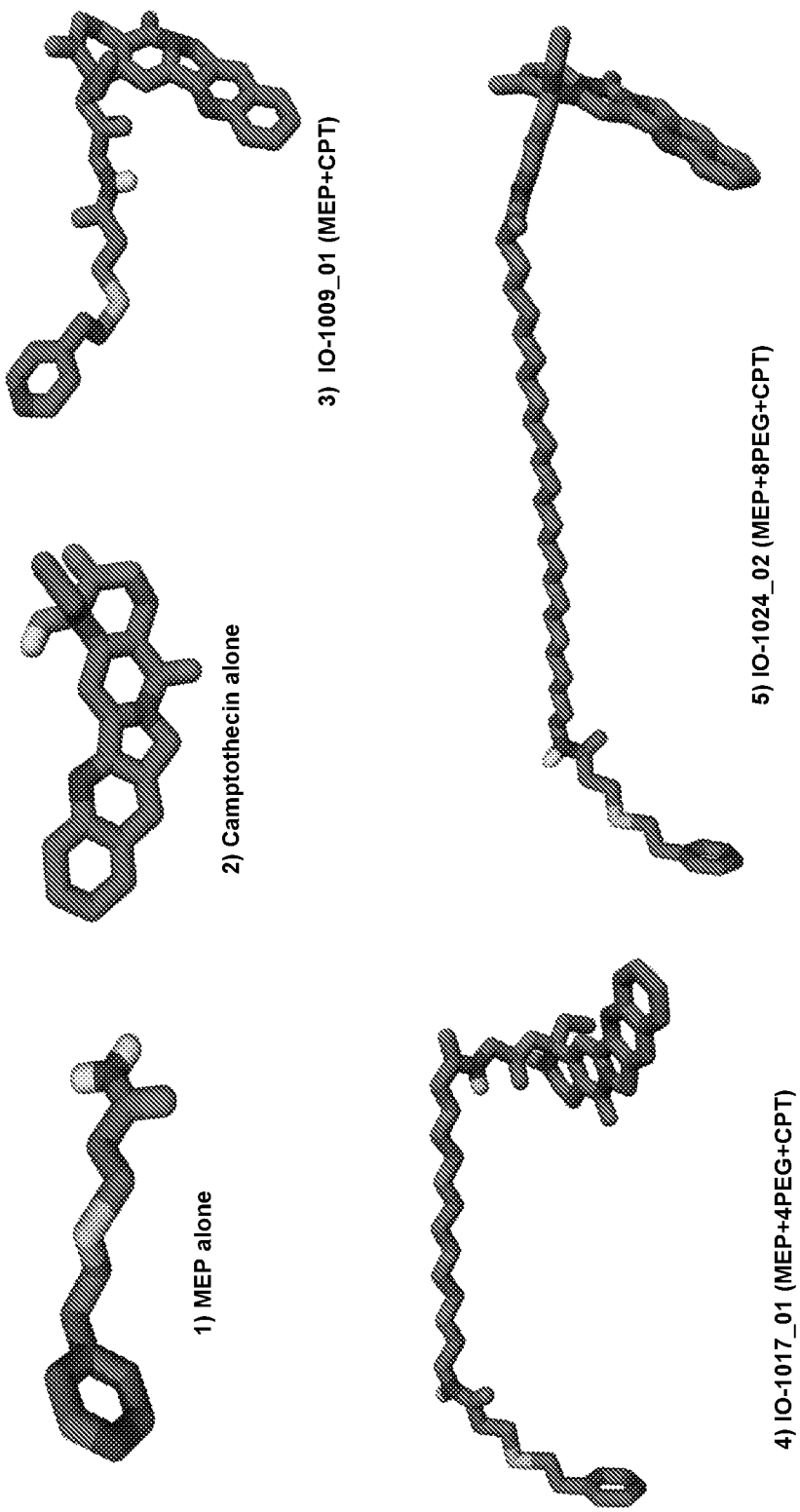
FIG. 9 shows chemical structures of exemplary ligand molecules investigated in this study.

Ligand Structure Optimization:

Quantum chemical geometry optimization of TO compounds was performed to obtain its lowest energy conformation. Further, short run MD simulations were performed with the geometry optimized structures. Different conformations were generated for these ligands by using MD simulations and quantum chemical calculations during the process of force field optimization. The initial optimized conformation of the molecules was depicted in FIG. 9. In-house Force field parameters were developed for the MEP, CPT and other MEP conjugated compounds for the classical MD simulations. The bonded and LJ-parameters were adapted from the CHARMM force field (Journal of Chemical Theory and Computation, 8: 3257-3273, 2012, Journal of Physical Chemistry B 102: 3586-3616, 1998, Journal of Computational Chemistry, 25: 1400-1415, 2004). Parameters for the dihedral angles and partial charges on each atom of the ligands were computed using quantum chemical calculations.

Docking:

Molecular docking is one of the main computational technique to get a predictive protein ligand complexes (BMC Bioinformatics 2013, 14(Suppl 14):S6). All of the docking calculations were carried out by using Autodock Vina 1.1.2 (J Comput Chem; 31:455-461). The choice of Autodock Vina for docking studies was directed by its ability to retain its efficacy for a greater number of rotational bonds and predict the near bioactive conformations with high level of accuracy (PLoS One, 2010 e11955). Here, we performed a flexible ligand docking with the rigid antibody, Fc fragment structure. Autodock Tools 1.5.6 (J Mol Graphics Mod, 1999, 17, 57-61) was used to extract the crystalline water and chain B from 1FC1 crystal structure. The polar hydrogens were assigned, Gasteiger charges were added and the rigid protein structure was saved in the PDBQT format. Similarly for the ligands, energetically favourable conformations were selected for the docking from the results of quantum chemical optimization, MD simulations and conformational analysis. The nonpolar hydrogens were merged and the Gasteiger charges were added. The flexibility of ligand was introduced by allowing the max number of torsions present in the molecule. Finally, the structures were saved in the PDBQT format to perform docking studies with 1FC1-A. The bigger ADC structures which exceeds the total number of permeable rotational bonds by Vina (tolerate up to 32 bonds), were docked individually with their defined grid spaces and the number of flexible bonds were limited by constraining some of the torsions present in the molecules. Docking grid size of 16 Å×22 Å×26 Å was used for the search space for the smaller ligand structures. In case of larger molecules the grid space parameters were changed on the basis of ligand size (end to end atoms distance of the ligand). The grid size was selected in order to allow the whole ligand molecule to scan possible conformations. The same grid dimensions were taken for all the other reported MEP binding sites Table 1, particularly for IO-1017_01 where we performed all site simulations. For each binding site the center of co-ordinates was obtained from the center of mass of active site residues. Each docking calculation, 10 poses were ranked according to the Autodock Vina scoring function. The docking results were assessed based on their energy criteria, the conformations with the best estimated free energy of binding were selected for further MD simulations and analysis.

Md Simulations:

A short run of MD simulations was performed by using the same simulated conditions during the process of force field evaluation conformations generation. Initial energy minimization was followed by a 500 ps NPT solvent simulation except for IO-1017_01 and MEP alone, CPT alone where we performed 100 ps of NVT simulations under vacuum conditions. The temperature was maintained at 300 K using Nose-Hoover thermostat. The vacuum or solvent MD simulations were selected based on the method of Quantum chemical geometric optimization. To make the structural comparisons under similar optimized conditions, the solvent quantum chemical optimized systems were simulated with the solvent molecules and for the non-solvent systems, MD simulations were performed under vacuum condition. Similarly for the protein-ligand complex systems, separate simulations were performed for each of the six mep binding sites shown in the Table 1 for the IO-1017_01 molecule initially. For all other compounds like MEP, CPT and designed MEP linker simulations were restricted to site 1. All the simulations were performed using Gromacs 4.6.7 (J Chem Theory Comput, 2008, 4, 435-447). For each simulation setup, the protein-ligand complex was first placed in a cubic simulation box maintaining a 2 nm distance with the box walls. Then the complex was solvated with TIP3P model water molecules. 4 chloride counter ions were added to maintain the electro neutrality of the protein-ligand complex system. All the bonded and non-bonded interaction potential parameters for protein were adapted from the CHARMM force field (Journal of Chemical Theory and Computation, 8: 3257-3273, 2012, Journal of Physical Chemistry B 102: 3586-3616, 1998, Journal of Computational Chemistry, 25: 1400-1415, 2004). Then the solvated systems were energy minimized using a steepest-descent algorithm. After energy minimization, NPT simulation was performed for 1000 ps keeping the protein-ligand complex position restrained by force constant of 1000 kJ/mol as implemented in Gromacs 4.6.7. The explicitly added water molecules were allowed to relax the unfavourable contacts between the protein and with the other water molecules. Following this 1 ns restrain simulation, a 200 ps NPT simulation was carried out by removing the position restrain on ligand, and maintaining the position restrain on backbone protein atoms with 1000 kJ/mol as implemented in the gromacs 4.6.7. The simulations were continued with the step by step removal of protein back bone atoms in the order of 800, 500, 250, 100, 50 and 1 kJ/mol respectively. At each step, 100 ps of NPT run were performed. These position restrained simulations allow the water molecules near the protein surface to equilibrate resulting in better solvation of the protein-ligand complex. This equilibration protocol was followed for all the MEP linked IO compounds with 1FC1-Fc fragment.

Finally, a 5 ns production run, NPT simulation was performed without any position restrain on ligand-protein (1FC1-A) complexes. P-LINCS algorithm (J. Chem. Theory Comput. 2007, 4, 116-122.) was used to constrain all the covalent bonds and time step of 2 fs was used for all the simulations. Electrostatic interactions were taken care of by PME (J. Chem. Phys. 1995, 103, 8577-8593) method with cut off of 1.2 nm, and van der Waals interactions were switched off between 1.0 to 1.2 nm. Pressure was kept constant at 1 bar using Parrinello-Rahman barostat (J. Appl. Phys. 1981, 52, 7182-7190) and temperature was fixed at 300 K using Nose-Hoover thermostat (J. Chem. Phys. 2007, 126, 014101).

Results and Discussion
  Sequence Analysis:
  From the resultant PSI-BLAST search we selected the 1FC1 as a template of cetuximab Fc fragment. 1FC1 has 97% sequence identity with the Cetuximab sequence. The simulation studies with 1FC1 helps us to validate our produced results with the Lin et al. (J. Phys. Chem. B 116, 1393-1400 (2012)). The molecular structure of the Fc fragment of IgG with PDB ID 1FC1 (J. Biochemistry 1981, 20, 2361-2370) was obtained from the Protein Data Bank (PDB). 1FC1 consists of two chains of A and B with CH2-CH3 constant domains of IgG1, which are identical in the amino acid sequence and are similar in the 3D structure (J. Biochemistry 1981, 20, 2361-2370). Therefore, only chain A of 1FC1 (defined as 1FC1-A) was considered here for further studies.

Ligand Optimization:
  All the ligands were optimized by following force field optimization protocol. As a part of the protocol, initially the force field parameters were developed individually for both MEP and Camptothecin fragments. After validation of the developed parameters, the respective parameters were implemented in the IO series ADC molecules. The basic structural formula of MEP linked ADC compounds were (MEP-CPT) and MEP-(n) PEG-CPT. The molecular series mainly differs in the number of PEG units between MEP and CPT fragments. Apart from the MEP, CPT fragments the designed ADC the molecules are IO-1009_01 (MEP+CPT), IO-1017_01 (MEP-4PEG-CPT) and IO-1024_02 (MEP-8PEG-CPT) contains no PEG, 4PEG and 8PEG units respectively. The obtained most stable conformations with lower energy values for IO-1009_01, IO-1017_01 and IO-1024_02 energies are reported in FIG. 10. For the ligands MEP and CPT the initial optimized structures were found to be energetically favourable conformations which are reported in FIG. 9. Structural overlap among the structures obtained from the short MD and that obtained after QM optimization were depicted in FIG. 11 for the investigated compounds. The structural overlap of MEP alone, CPT alone and other MEP linker compounds with their QM optimized structures indicate that the developed force field is capable of reproducing the structural features for these molecules. This is further validated by computing the RMSD of the structures as a function of time over 500 ps. Lowest RMSD indicates that the structural features from QM optimization are preserved during MD simulations. The RMSD values are shown in FIG. 12 for all the simulated molecules. The peg units connecting MEP fragment and CPT fragment offering a greater flexibility in IO-1024_02 than in IO-1017_01. The more number of flexible peg units in IO-1024_02, causing a molecule to attain a bent conformation, where MEP and CPT parts are closed to each other. In the closed conformation there is probability for pi-pi stacking interaction of the MEP pyridine ring with CPT aromatic rings. But, there is no such observable pi-pi stacking interactions between groups in the bent conformations, as the two groups are not in a pi-pi interacting distance range. The structural overlap and RMSD values of 4PEG and 8PEG MEP linkers with their quantum chemical optimized structures were shown in FIGS. 9 and 12 respectively.

Docking:
  Docking studies were performed with 1FC1-A Fc fragment by taking energetically stable conformation. Initial studies were performed with MEP and CPT alone and further proceeded with IO-1009_01, IO-1017_01 and IO-1024_02. The top scoring conformations of MEP linked compounds on site 1 were found to contain 4-MEP part inside the cavity FIG. 13. It indicates that the Camptothecin part has low affinity for the MEP binding sites reported by Lin et al. Apart from these MEP linkers, CPT alone, docking was also performed on the Site 1. The docking calculations were continued to the other reported MEP binding sites for the IO-1017_01 ligand. Tens of dock poses were collected from the Autodock Vina, but the energy gap between the two adjacent poses were differed by only 0.1 and 0.2 Kcal/mol, and sometimes the energy difference between the highest to lowest rank poses were found to be not more than 2 Kcal/mol. Similar results were also observed during the comparison of docking scores with the other MEP binding sites as well as with the other ADC-MEP linker molecules. One of the main reasons for these kinds of observations was assumed to be the structural similarity of the docked molecules. Apart from these structural similarities between the ligands some of the other possible factors include the total number of rotational bonds, number of grid points specified on the protein, and the number of residues covered under grid will also interfere with the results during the scoring evaluations by using various scoring functions. Here, in all the cases, MEP is the main moiety where it can go and fit well into the binding pocket due its hydrophobic nature and its interactive pyridine ring. But in the case of camptothecin, less number of rotational bonds gives a higher docking score in comparison the MEP alone under same grid dimensions.

These observations from this docking analysis led us to perform MD simulations and binding free energy calculations to understand the basic molecular interactions between protein and ligand. All the protein (1FC1-A)-ligand complexes were further used to perform MD simulations.

Figure 13:
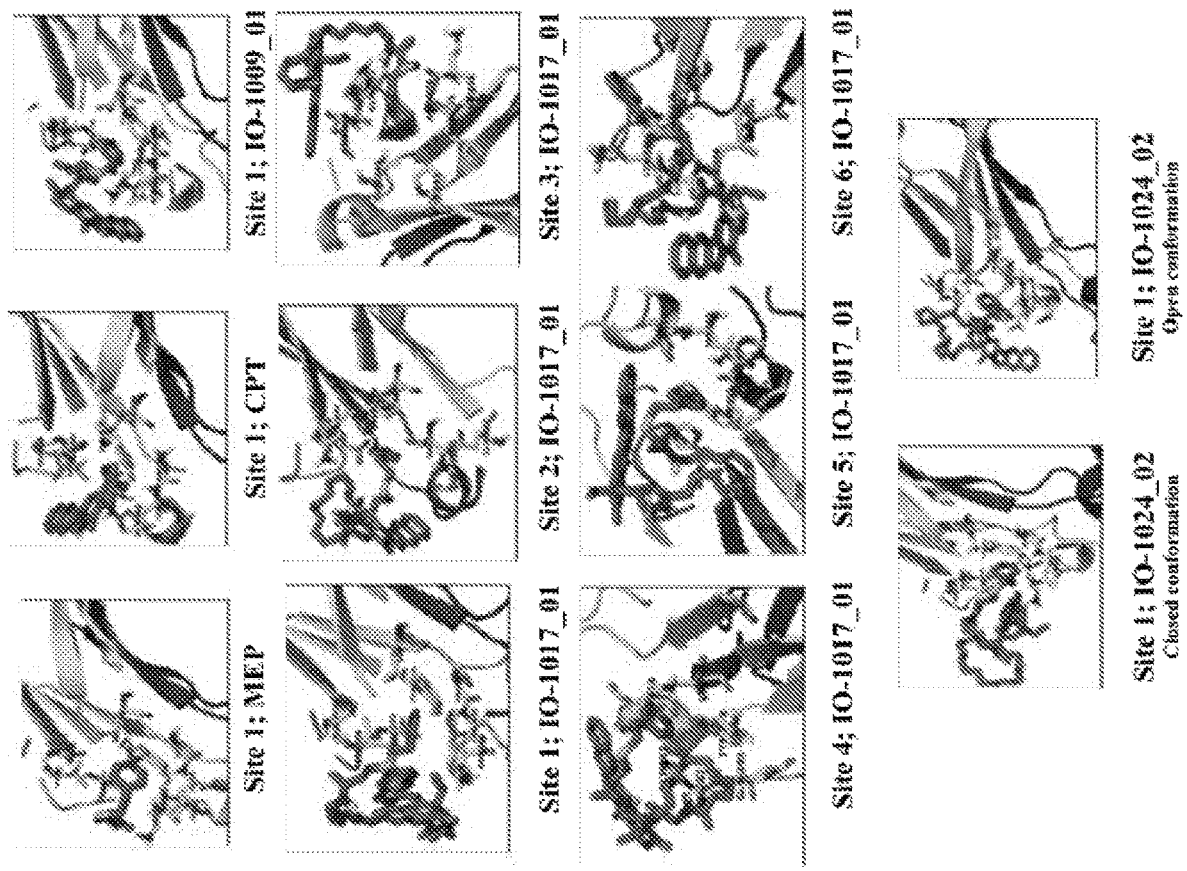
FIG. 13 shows snapshots of antibody-ligand complex structures before MD simulations.
Figure 14:
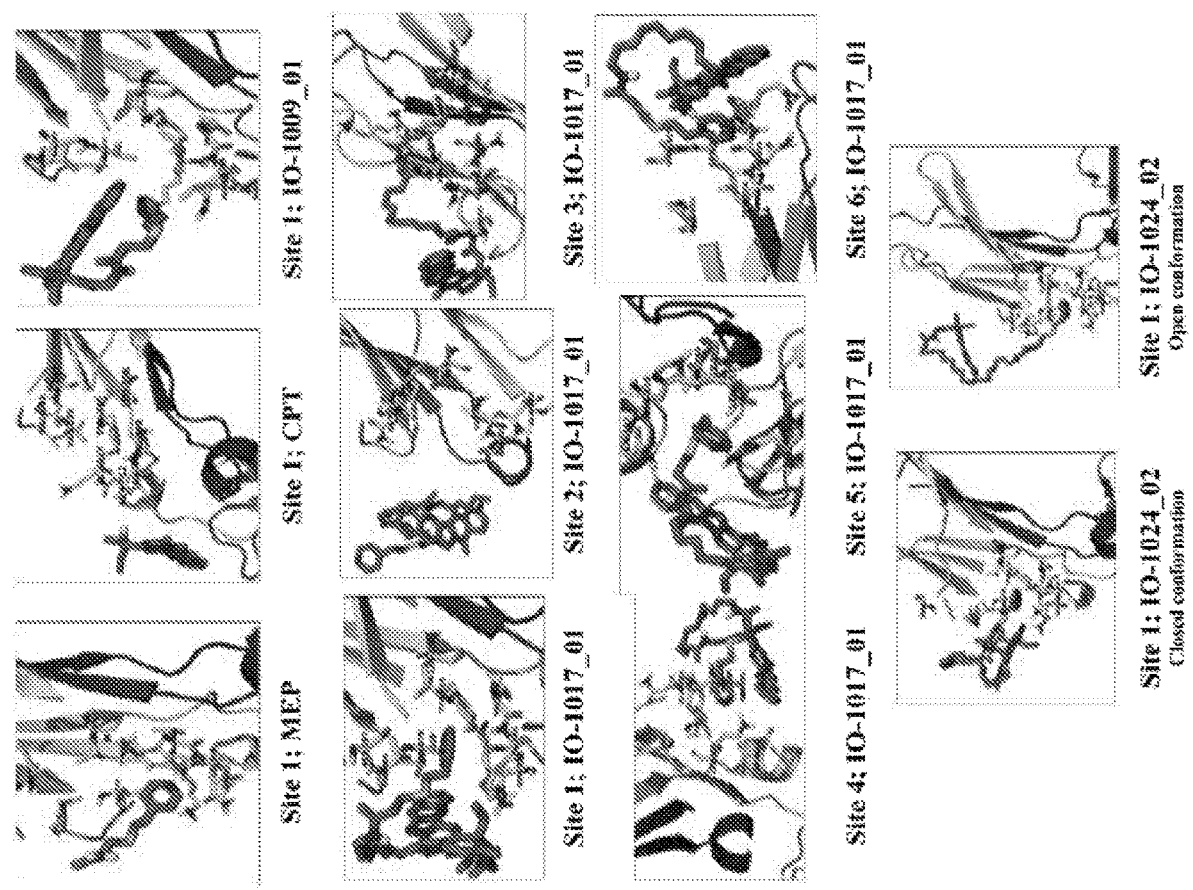
FIG. 14 shows snapshots of antibody-ligand complex structures 5 ns of MD simulations.
Figure 16C:
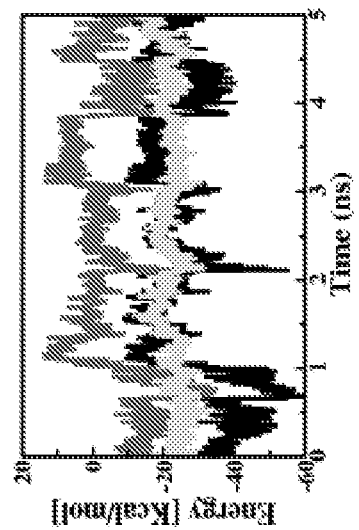
FIGS. 16A-16C show the non-bonded interactions for MEP alone (FIG. 16A), CPT alone (FIG. 16B) and IO-1009_01 (FIG. 16C).
Figure 15G:
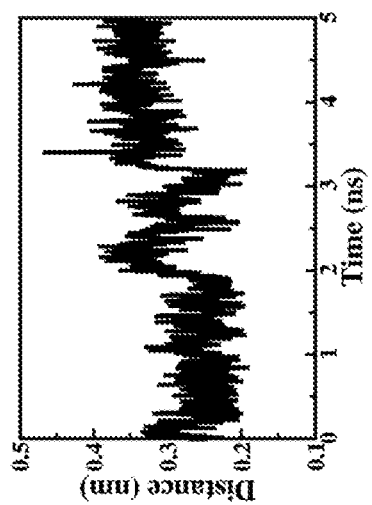
Figure 16B:
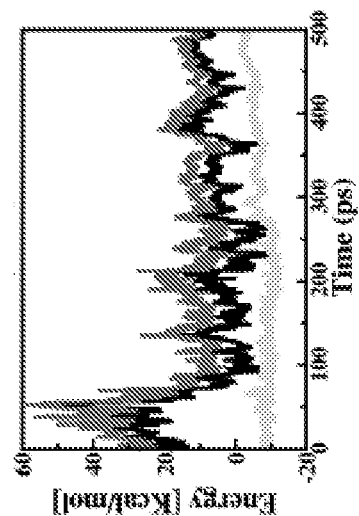
Figure 16A:
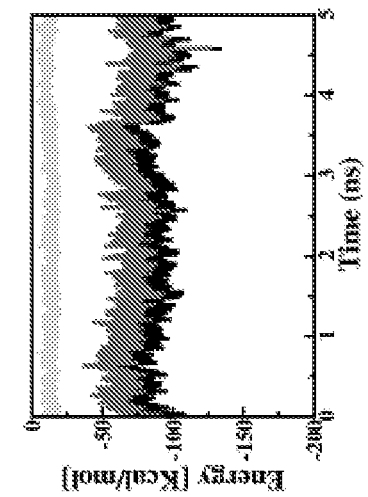
Figure 17A:
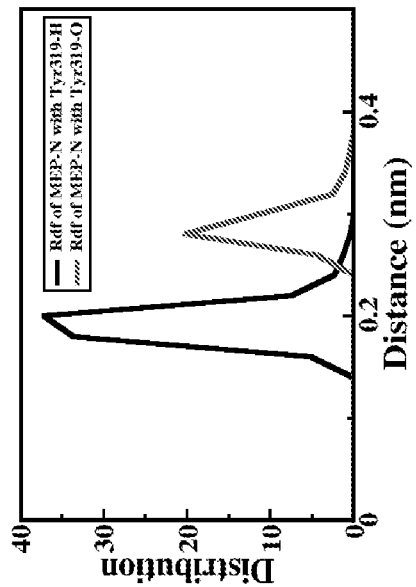
FIGS. 17A-17D show distance distribution calculations for MEP alone (FIG. 17A), IO-1017_01 (FIG. 17B), IO-1022_02 (Closed conformation) (FIG. 17C) and IO-1022_02 (open conformation) (FIG. 17D)
Figure 17B:
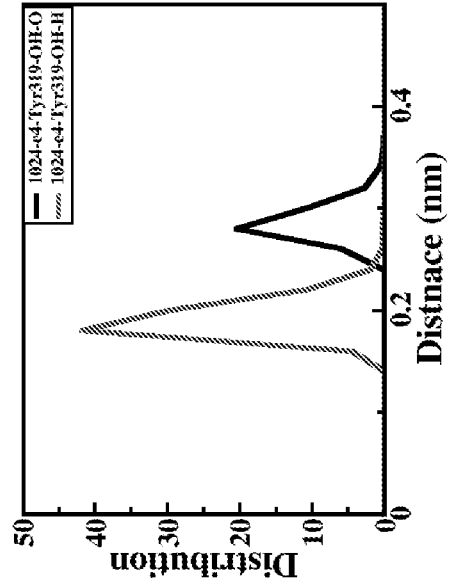
Figure 17C:
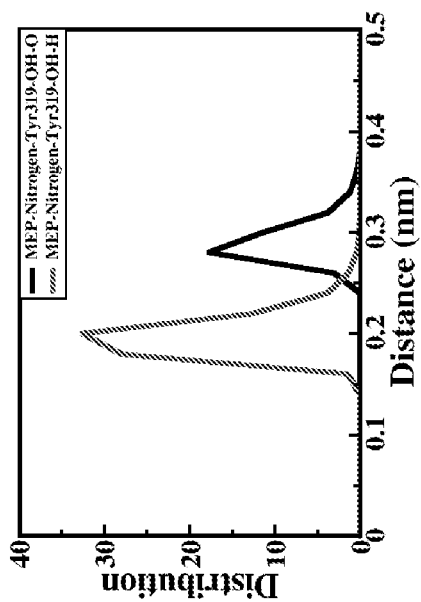
Figure 17D:
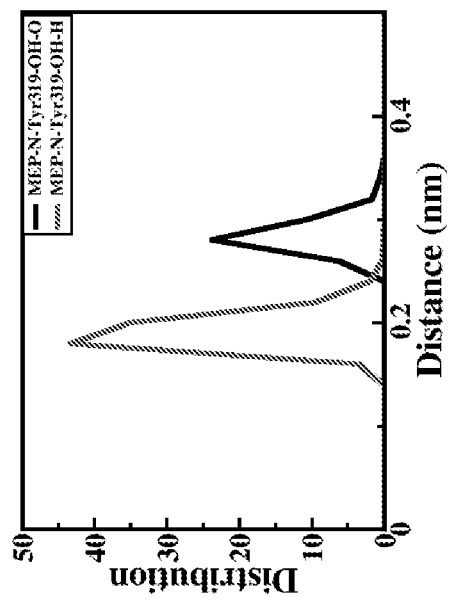
Figures 18A, 18B, 18C, 18D, 18E, 18F:
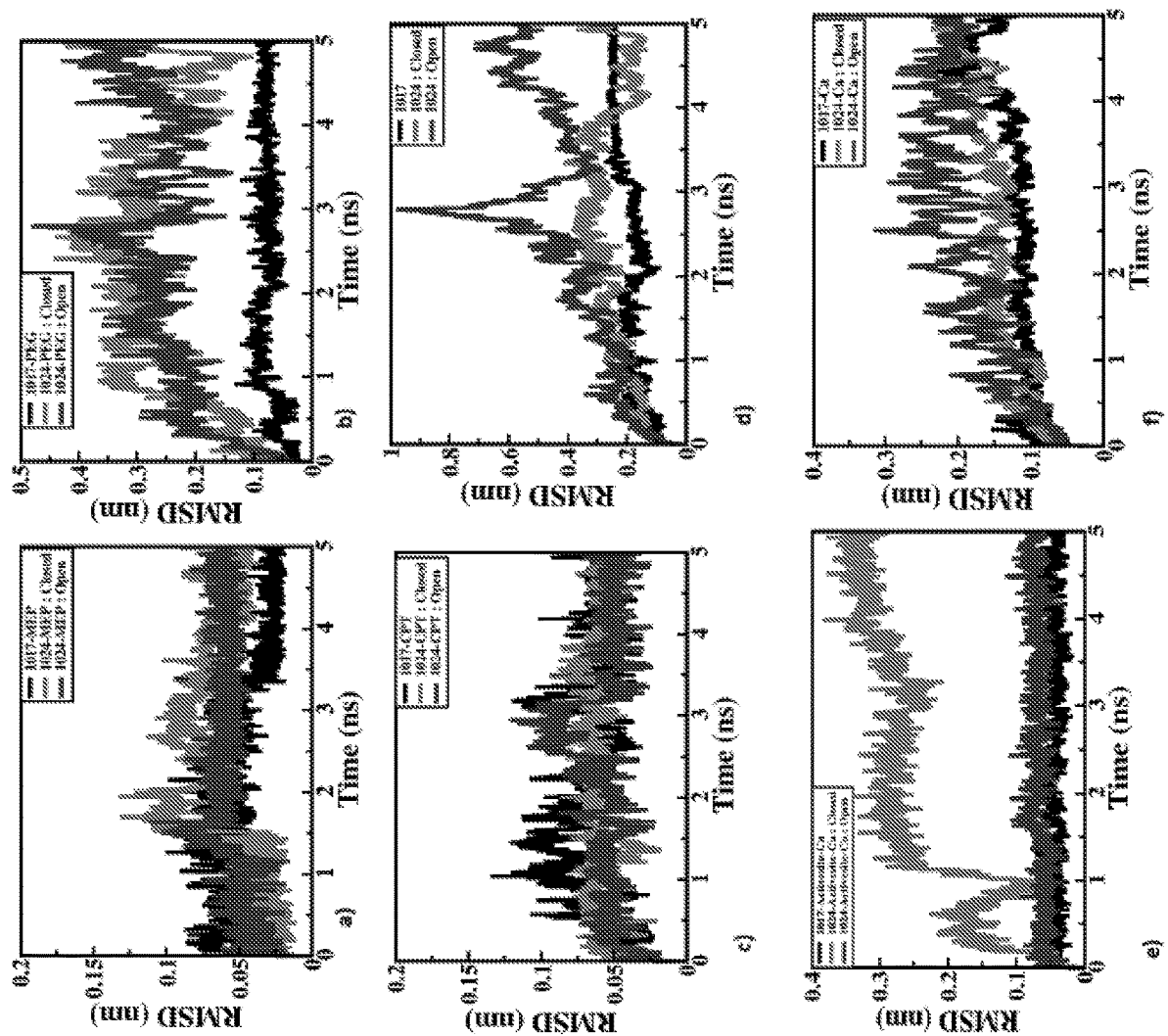
FIGS. 18A-18F show the ligand and protein fluctuations in 4 PEG and 8 PEG simulations: MPE Rmsd (FIG. 18A), PEG Rmsd (FIG. 18B), CPT Rmsd (FIG. 18C), whole ligand Rmsd (FIG. 18D), active site Ca Rmsd (FIG. 18E) and backbone Rmsd (FIG. 18F)

MD Simulations:

MD simulations are used to evaluate the binding stability and binding possibility of ADC molecules with the Antibody in ADC-Antibody complex system. The dynamic interactions and molecular events were evaluated for all the compounds with the antibody during MD simulations. Snapshots of before and after 5 ns production run were depicted in FIGS. 13 and 14 for all the simulations. After 5 ns, in MEP alone MD simulations the MEP molecule stays nearer to the active site but in the case of CPT within 500 ps it is falling off from the antibody. The unfavourable electrostatic interactions were observed between the camptothecin and antibody Fc fragment during the MD simulations. The lack of structural complementary on the CPT makes the molecule becomes non-interactive and causes it to move away from the active site. The Center of Mass (CM) distances between the CM of the active site and CM of both MEP and CPT were calculated as a function of time throughout the MD simulations were reported in FIG. 14. The lesser deviation in the CM distance of the MEP alone complex system shows that MEP is staying near the active site throughout 5 ns MD simulations. The favourable electrostatic and van der Waal interactions of MEP with the antibody Fc fragment showing that the MEP substrates have a greater binding affinity with the site 1. These produced results were in comparison with the Lin et al. simulation studies (J. Phys. Chem. B 116, 1393-1400 (2012)). These comparative results help us to validate our further MEP conjugated molecular simulations. The Non-bonded interactions were calculated for both MEP and CPT separately by excluding solvent molecules with the in-house developed program, which were depicted in FIGS. 16A-16C. Apart from these non-bonded interactions a hydrogen bond was also observed between TYR319 side chain hydroxyl group with an MEP pyridine ring which is in correlation with Lin et al. (J. Phys. Chem. B 116, 1393-1400 (2012)). The Distribution of distance between MEP nitrogen and TYR319 side chain —OH hydrogen fall within H-bonding distance represented in FIGS. 17A-17D show an H-bonding interaction between MEP nitrogen of MEP-NH2 and TYR319. This stable H-bonding interaction contributes to the constant CM distances of MEP in MEP alone simulation. The structural integrity of protein in protein-ligand complex system was analyzed by using DSSP analysis using. The secondary structure was maintained throughout the simulation without any major effective changes. Similarly the RMSD values of protein backbone and ligands were also calculated to measure the structural deviations during MD simulations. The lower RMSD values of both protein and ligand represents, there is no observable structural changes in the protein-ligand complex system. These molecular level insights and favorable interactions of these MEP substrates, helps us to continue our further studies with the newly designed MEP-ADC linkers IO-1009_01, IO-1017_01 and IO-1024_02. The simulation results of IO-1009_01, observed that the molecule IO-1009_01 is showing favorable interactions for the initial 1 ns simulation time. As the simulation progress the molecule starts moving away from the active site. Similar to the MEP alone simulations the CM distances were calculated though out 5 ns between the CM of MEP pyridine ring of IO-1009_01 and CM of Site 1 active site residues. The initial lower CM distances show that, for the first ns the molecule stays inside the cavity and further increases in the CM distances will impart that the IO-1009_01 coming out from the cavity. Without wishing to be bound by a theory, these sudden changes can appear due to the close contact of the directly linked CPT of MEP+CPT with the protein antibody since it is already demonstrated that CPT exerts positive electrostatic interactions when it comes nearer to the protein. But for the initial 1 ns it is observed that the favorable MEP non-bonded interactions and hydrogen bonding with the protein keep the molecule to stay within the cavity. Later on, due to the dominated positive electrostatic interactions of CPT causes the whole ligand to move away from the cavity. These kind of observations with IO-1009_01 defined us to the addition of spacer linker between MEP and CPT. So that the interacting MEP group can be separated by a certain distance with the CPT, thus we can minimize the unfavorable effects produced by the CPT. If the CPT is separated by a distance of greater than 1.2 nm we can able to achieve some effective results with these MEP linkers. Based on the above, PEG molecules were selected as a spacer linker, and PEG helps us to increase the solubility of the molecule. IO-1017_01 (MEP+4PEG+CPT) and IO-1024_02 are the molecules with these PEG spacer linkers. The 5 ns MD simulations of IO-1017_01 were analyzed similar to MEP alone MD simulations. Initially the simulation was performed on Site 1 with IO-1017_01. The prominent results from the Site 1: IO-1017_01 simulations encouraged us to extend the simulations with all other MEP binding sites. The cumulative analysis of all the six MEP binding sites with IO-1017_01 is discussed below. The snapshots of before and after 5 ns simulations of IO-1017_01 with 6 different binding sites are represented in FIGS. 13 and 14 respectively. The MD simulations showed that the IO-1017_01 capable to bind four of the reported binding sites where MEP is nearer to the binding cavity throughout the MD simulation. These sites were found to be as Site 1, Site 3, Site 4, and Site 6.

Figure 15C:
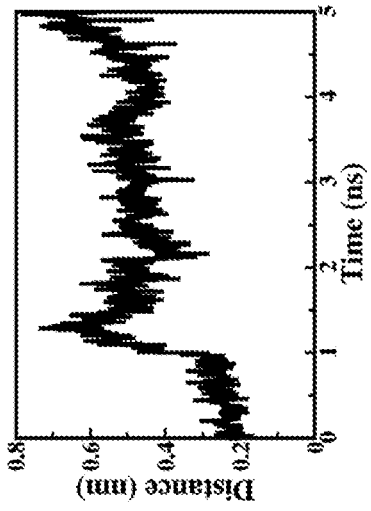
FIGS. 15A-15G show the CM distance MEP inside the active site: MEP alone (FIG. 15A), CPT alone (FIG. 15B), IO-1009_01.
Figure 15B:
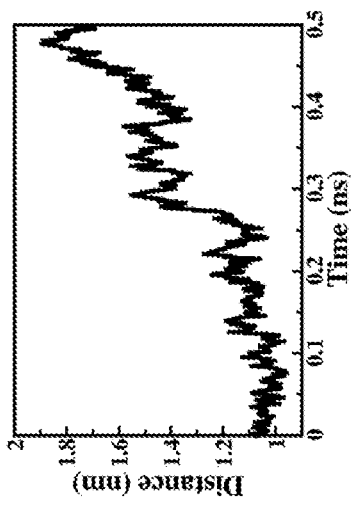
Figure 15A:
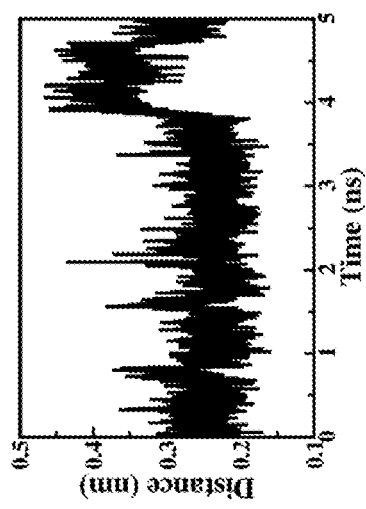
Figure 15F:
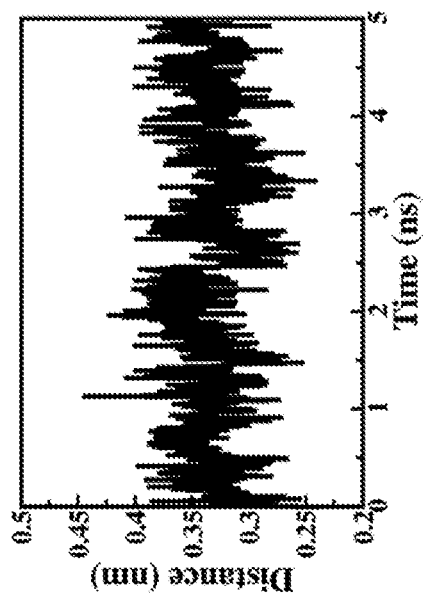
Figure 15E:
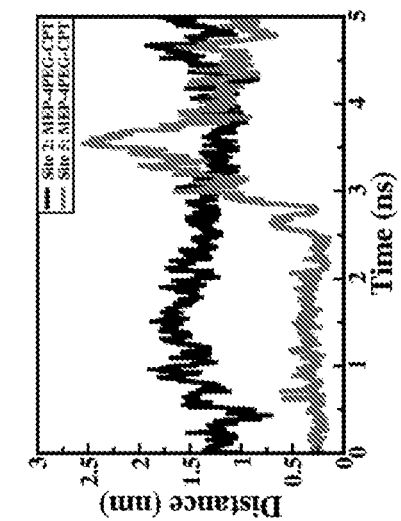
Figure 15D:
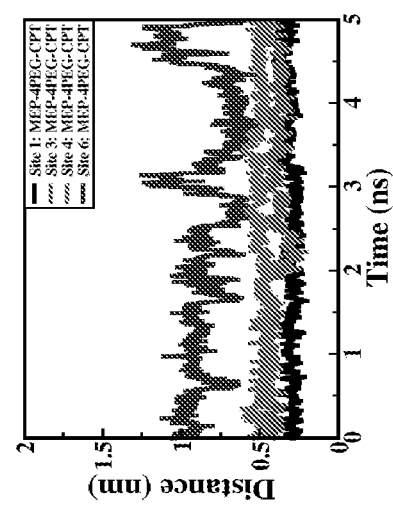
Figure 19C:
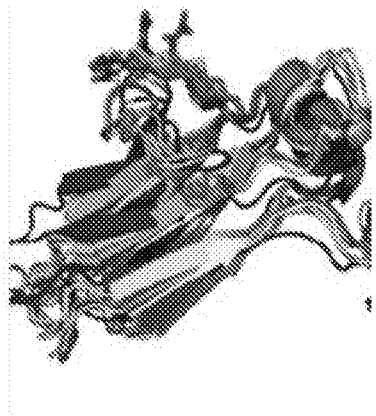
FIGS. 19A-19C show snapshots of ligand binding site 1: 10-1017_01 (FIG. 19A), IO-1024_02 (closed conformation) (FIG. 19B) and IO-1025_02 (open conformation) (FIG. 19C). Only MEP part is shown for clarity.
Figure 19B:
Figure 19A:
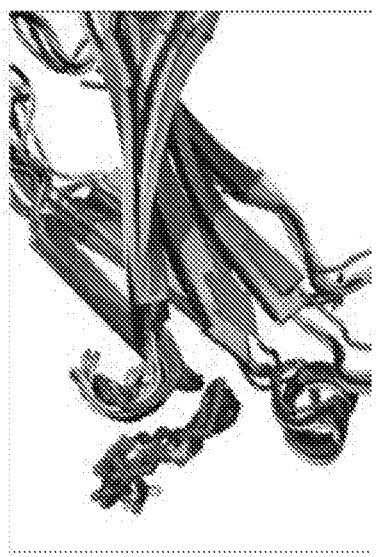
Figure 20A:
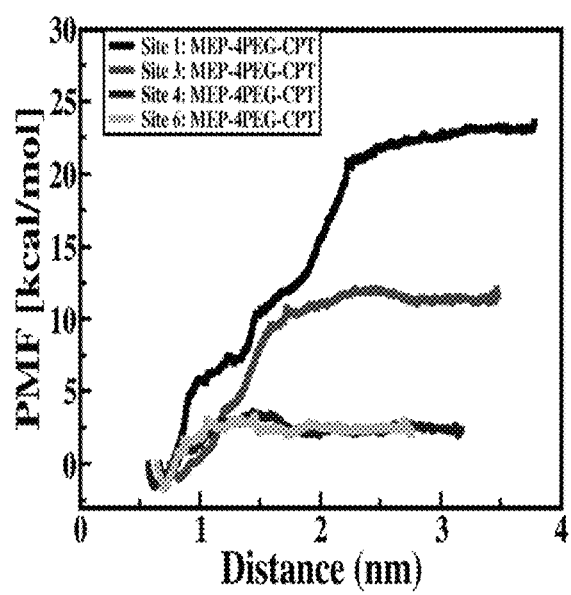
FIGS. 20A and 20B show PMF calculations for IO-107_01 (FIG. 20A) and IO-1024_02 (FIG. 20B).
Figure 20B:
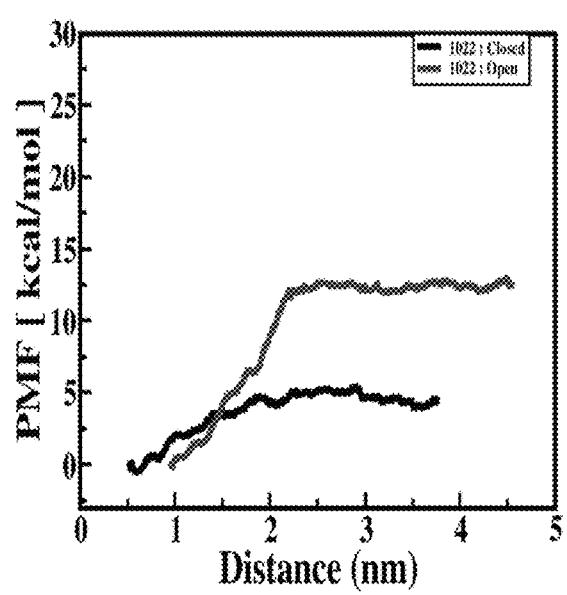

The ligand remains at the binding sites 1, 3, 4, and 6 during the 5 ns production run implying higher affinity of these sites for the ligand IO-1017_01. At Site 2 it was found that molecule comes out from the cavity during the step by step removal of protein restrain during the MD simulations. But in the case of Site 5 it was found to be that MEP moves partially away from the active site due to lack of proper interactions with the active site residues for the IO-1017_01 molecules. It is evident that the ligand comes out of the binding sites 2 and 5 during the 5 ns production run for IO-1017_01. It indicates that the binding affinity of these sites for ligand IO-1017_01 is low. Thus, the Site 2 and Site 5 were discarded for further studies and analysis. The CM distances were calculated and are depicted in FIGS. 15D and 15E for IO-1017_01 with all 6 binding sites. The CM distance is least for the site 1 throughout 5 ns it is observed that the lower CM distances were mainly due to the above discussed favorable non-bonded interactions of MEP with protein and H-bond interactions of MEP pyridine nitrogen with the Site 1, Tyr 319 residue. For site 3, CM distance fluctuates close to CM distance of site 1. For Site 4, CM distance is higher than the Sites 1 and 3. For site 6, it is highest and fluctuating. It indicates that at site 6 it is in loosely bound conformation. The CM distance at site 2 is high from the starting and does not decrease during the simulation time (as seen for site 6, where the distance fluctuates). At site 5 during the 5 ns we can see the distance variations with the ligand showing some outward movement from the antibody. Similar to above mep simulations at site 1, distribution of distance between MEP nitrogen and Tyr319 side chain —OH hydrogen fall within H-bonding distance shown in FIGS. 17A-17D. It shows a possible H-bonding interaction between MEP nitrogen on MEP-4PEG-CPT and Tyr319 which contributing a constant CM distance at site 1. There is no observable particular hydrogen bonding of IO-1017_01 with the other binding sites (Site 3, Site 4 and Site 6) where the ligand is present near cavity throughout the simulation. Because of its favorable non-bonded interactions with the antibody keep the IO-1017_01 molecule nearer to the cavity for the mentioned site 3, site 4 and site 6. Similarly the PEG molecules also not showing any kind of hydrogen bonding interactions with the antibody but there is a small, favorable non-bonded interactions were observed with the protein. No significant changes were observed in the secondary structures of antibody Fc fragment in simulations with IO-1017_01 with all the MEP binding sites. IO-1024_02 is similar to IO-1017_01 with an increase in the number of PEG units. It has 8PEG spacer linker unlike to IO-1019_01 which is a 4PEG linker. Two 5 ns, MD simulations were completed for IO-1024_02 by simulating the two possible conformations with the Site 1. The same CM distances and distance distribution properties were calculated for both IO-1024_02 simulations to compare with other MEP linkers. In IO-1024_02 open system where CPT is at a larger distance showing better interactions than the closed conformation. The CM distances were calculated, similar to the above calculations, showing that the MEP is staying inside the cavity throughout the simulation for both the conformational simulations. A Small increased distance was observed in the closed conformation of IO-1024_02 because of its CPT lying nearer to MEP, able to interfere with the MEP protein interactions. In the extended IO-1024_02 conformation the MEP is interacting freely as similar to IO-1017_01. The distribution of distance between MEP nitrogen and TYR319 side chain —OH of hydrogen at site 1 falls within H-bonding distance. It shows a possible H-bonding interaction between MEP nitrogen on MEP-8PEG-CPT and TYR319. The calculated RMSD values for the ligand IO-1024_02 showing higher fluctuations than the IO-1017_01. The increased number of flexible PEG units, making the molecule more flexible and causing higher fluctuations during MD simulations. The comparative analysis of these fluctuations between 4 PEG and 8 PEG simulations are shown in FIGS. 18A-18F. These higher fluctuations in the molecule affecting the interaction of MEP inside the cavity were observed. To observe these changes different snapshots of ligand binding with the site 1 are depicted in the FIGS. 19A-19C for the IO-1017_01 and IO-1024_02 molecules. The observations from the FIGS. 19A-19C show that the ligand IO-1017_01 was comparatively binded well to the site 1 with respect to IO-1024_02. To further quantify and compare the affinity of different ligands and the different binding sites we have performed free energy calculations using the umbrella sampling method (J. Phys. Chem. B 2010, 114, 1652-1660) as implemented in Gromacs 4.6.7. Free energy of binding indicates how efficiently a ligand binds to a cavity. For this, output configuration from 5 ns production run was chosen for all the four mentioned sites for the ligand IO-1017_01 and site 1 for the ligand IO-1024_02 from both conformations, and the ligand was pulled with a velocity of 10 nm ns$^{-1}$ by applying a harmonic potential to its center of mass (COM) with force constant of 1000 kJ/mol/nm$^2$. Different frames were extracted from pulling simulation at certain intervals (based on overlap of histograms) of COM distance between pulled chain and reference group. 500 ps of the umbrella sampling, production run were performed on each configuration by applying the same harmonic potential used during pulling and taking initial COM distance as reference. Then the weighted histogram analysis method (WHAM) (J. Chem. Theory Comput. 2010, 6, 3713-3720) was used to calculate the potential of mean force (PMF) by analyzing the simulation trajectories of each umbrella windows. PMF as a function of distance is depicted in FIGS. 20A and 20B for all the simulations. PMF is highest for site 1 with IO-1017_01, implies a highest binding affinity of the IO-1017_01 molecule with the site 1. This is followed by site 3, and then sites 4 and 6 for IO-1017_01 ligand. Order of binding affinity of these MEP-4PEG-CPT at the different sites is also same. PMF values for the ligand IO-1024_02 comparatively lower than the IO-1017_01 molecule for the site 1. The open conformation possesses higher binding energy value than the closed conformation. Binding free energy of ligand IO-1017_01 at sites 1, 3, 4, and 6 and IO-1024_02 calculated from PMF (FIG. 20) is summarized in Table 2. Binding free energy is highest for the ligand IO-1017_01 with site 1 which shows that the ligand binds best with site 1 compared to the other sites. Similarly, IO-1017_01 (MEP-4PEG-CPT) showed comparatively higher binding affinity than the ligand IO-1024_02 (MEP-8PEG-CPT). The stable Hydrogen bonding interaction of IO-1017_01 with the site 1, requires a more force to pull out from the active site. Even though same molecular interactions were also observed in the IO-1024_02, but the observed higher fluctuations effecting the interactions of MEP with the active site in a limited manner. Similarly for IO-1017_01 with the other binding site, the lack of proper strong bonding interactions of MEP with the binding site, causes the molecule easily pulled out from the cavity by less amount force. These less amounts of forces infers the weak affinity of ligand with the protein binding site. From Table 2 and FIG. 20 the order of binding free energy at different sites is as follows Site 1>Site 3>Site 4>Site 6 for IO-1017_01 and the order of binding affinity between the studied molecules were founded to be MEP-4PEG-CPT>MEP-8PEG-CPT (open)>MEP-8PEG-CPT (Closed).

TABLE 2

Binding free energy calculations:

| Molecule | Binding Free Energy (kcal/Mol) | | | |
| --- | --- | --- | --- | --- |
| | Site1 | Site3 | Site4 | Site6 |
| MEP-4PEG-CPT (IO-1017_01) | −24.63 | −12.14 | −3.96 | −3.33 |
| MEP-8PEG-CPT (IO-1024_02 Open conformation) | −17.28 | — | — | — |
| MEP-8PEG-CPT (IO-1024_02 Closed conformation) | −13.75 | — | — | — |

What is claimed is:
1. A method of evaluating and/or optimizing a supramolecular therapeutic, the method comprising:
 (a) calculating a quantum mechanics (QM) optimized matched structure for a subunit (therapeutic agent) of the supramolecular therapeutic using the steps:
  (i) optimizing geometry of said subunit using quantum mechanical methods;
  (ii) calculating a plurality of force field parameters from the optimized subunit of step (i);
  (iii) optimizing energy of the subunit using the plurality of force field parameters calculated in step (ii);
  (iv) optimizing geometry of the subunit of step (iii) via molecular dynamics (MD) simulation of said subunit in vacuum using the plurality of force field parameters calculated in step (ii); and

(v) comparing the optimized subunit of step (i) with the optimized subunit of step (iii), wherein, if the optimized subunits differ from each other, changing at least one of the plurality of force field parameters calculated in step (ii) and repeating steps (ii)-(v);

(b) calculating an all atomistic molecular dynamics simulation of said QM-optimized matched structure using the steps:

(i) forming a simulation cell by placing two of the said QM-optimized matched structures in a simulation cell parallel to z-axis of said simulation cell;

(ii) translating the said QM-optimized matched structures along x-axis of the simulation cell, thereby doubling a number of QM-optimized matched structure in the simulation cell;

(iii) optimizing energy of the simulation cell using a steepest descent/conjugate gradient method;

(iv) translating the QM-optimized matched structures in the simulation cell of step (iii) along the x-axis, thereby doubling the number of QM-optimized matched structures in the simulation cell;

(v) repeating steps (iii)-(iv) until number of QM-optimized matched structures in the simulation cell is half of a predetermined number N;

(vi) solvating the QM-optimized matched structures with an equilibrated box of lipid bilayer and water molecules, wherein number of lipid molecules in the lipid bilayer is half of a predetermined number M of lipid molecules;

(vii) minimizing energy of the simulation cell from step (vi) using a steepest descent/conjugate gradient method;

(viii) packing the lipids (optionally excipient molecules) and the QM-optimized matched structures by molecular dynamics simulation of the simulation cell of step (vii) with isotropic pressure coupling;

(ix) removing any additional empty spaces created inside the simulation cell;

(x) removing any water molecules from hydrophobic core of lipid bilayer;

(xi) translating the simulation cell of (x) to form a large simulation cell comprising N QM-optimized matched structures and M lipid molecules;

(xii) minimizing energy of the large simulation cell of (xi) using a steepest descent/conjugate gradient method;

(xiii) packing the large simulation cell of (xii) using a molecular dynamics simulation with isotropic pressure coupling; and (xiv) removing any water molecules from hydrophobic core of lipid bilayer;

(xv) packing the simulation cell of (xv) using a molecular dynamics simulation with semi-isotropic pressure coupling; and (c) comparing trajectory of simulation cell from step (b) with an upper bound trajectory and a lower bound trajectory, wherein the upper bound trajectory is a trajectory obtained with a pure lipid bilayer and the lower bound trajectory is a trajectory obtained with a lipid bilayer with a nonoptimized structure for the therapeutic agent;

(d) modifying structure of the subunit and repeating steps (a)-(d) unless trajectory is substantially close to the upper bound trajectory.

2. The method of claim 1, wherein the therapeutic agent is an antibody drug conjugate (ADC).

* * * * *